United States Patent
Marx et al.

(10) Patent No.: US 9,631,183 B2
(45) Date of Patent: Apr. 25, 2017

(54) DNA POLYMERASES WITH INCREASED SUBSTRATE SCOPE

(75) Inventors: Andreas Marx, Constance (DE); Nina Blatter, Bohringen (DE)

(73) Assignee: Universität Konstanz, Constance (DE)

( * ) Notice: Subject to any disclaimer, the term of this patent is extended or adjusted under 35 U.S.C. 154(b) by 0 days.

(21) Appl. No.: 14/420,089

(22) PCT Filed: Aug. 8, 2012

(86) PCT No.: PCT/EP2012/003388
§ 371 (c)(1),
(2), (4) Date: May 28, 2015

(87) PCT Pub. No.: WO2014/023318
PCT Pub. Date: Feb. 13, 2014

(65) Prior Publication Data
US 2015/0267182 A1    Sep. 24, 2015

(51) Int. Cl.
| | |
|---|---|
| C12N 9/12 | (2006.01) |
| C12N 15/00 | (2006.01) |
| C12N 1/20 | (2006.01) |
| C12P 21/06 | (2006.01) |
| C12P 21/04 | (2006.01) |
| C07H 21/04 | (2006.01) |
| C12Q 1/68 | (2006.01) |
| C12P 19/34 | (2006.01) |
| C12N 15/09 | (2006.01) |

(52) U.S. Cl.
CPC ........... *C12N 9/1252* (2013.01); *C12N 15/09* (2013.01); *C12P 19/34* (2013.01); *C12Q 1/6844* (2013.01); *C12Y 207/07007* (2013.01)

(58) Field of Classification Search
CPC ...... C12N 9/22; C12N 15/102; C12N 9/1252; C12P 19/34
See application file for complete search history.

(56) References Cited

U.S. PATENT DOCUMENTS

| | | |
|---|---|---|
| 2005/0250131 A1 | 11/2005 | Jestin et al. |
| 2011/0027833 A1 | 2/2011 | Hogrefe et al. |

FOREIGN PATENT DOCUMENTS

DE    10 2006 025 154 A1    12/2007

OTHER PUBLICATIONS

Branden et al. Introduction to Protein Structure, Garland Publishing Inc., New York, p. 247, 1991.*
Gloeckner et al. Evolving a Thermostable DNA Polymerase That Amplifies from Highly Damaged Templates. Angew. Chem. Int. Ed. 2007, 46, 3115-3117.*
Vichier-Guerre et al. A Population of Thermostable Reverse Transcriptases Evolved from Thermus aquaticus DNA Polymerase I by Phage Display. Angew. Chem. Int. Ed. 2006, 45, 6133-6137.*
Sauter et al. Evolving Thermostable Reverse Transcriptase Activity in a DNA Polymerase Scaffold. Angew. Chem. Int. Ed. 2006, 45, 7633-7635.*
Obeid et al., "Interactions of non-polar and "Click-able" nucleotides in the confines of a DNA polymerase active site," *Chem. Commun.*, 2012, 48:8320-8322.
Kranaster et al., "One-step RNA pathogen detection with reverse transcriptase activity of a mutated thermostable *Thermus aquaticus* DNA polymerase," Biotechnol. J., 2010, vol. 5, No. 2, pp. 1-8.
Obeid et al., "Learning from Directed Evolution: *Thermus aquaticus* DNA Polymerase Mutants with Translesion Synthesis Activity," *ChemBioChem*, 2011, 12:1574-1580.
Kranaster et al., "Engineered DNA Polymerases in Biotechnology," *ChemBioChem*, 2010, 11:2077-2084.
Sauter et al., "Neue Enzymeigenschaften durch gerichtete Evolution: Entwicklung and Charakterisierung einer thermostabilen Reversen Transkriptase aus einer DNA-abhängigen DNA-Polymerase," Dissertation, Aug. 2007, XP002689477, [http://kops.ub.uni-konstanz.de/bitstreuter_Diss.pdf?sequence=1].

* cited by examiner

Primary Examiner — Yong Pak
(74) Attorney, Agent, or Firm — Riverside Law LLP

(57) ABSTRACT

The present invention relates to DNA polymerases displaying increased substrate scope such as improved reverse transcriptase and DNA polymerase activities, as well as improved activities for incorporating and extending modified nucleotides. In particular, the present invention relates to DNA polymerases derived from wild-type *Thermus aquaticus* (Taq) polymerase, comprising the mutations S515R, I638F, and M747K with regard to the wild-type amino acid sequence. The present invention further relates to nucleic acids coding for the DNA polymerases of the present invention, vectors containing said nucleic acids, host cells containing said vectors or nucleic acids, methods for the generation of DNA molecules using said DNA polymerases, kits containing said DNA polymerases, and uses thereof.

18 Claims, 10 Drawing Sheets

A

Figure 1:
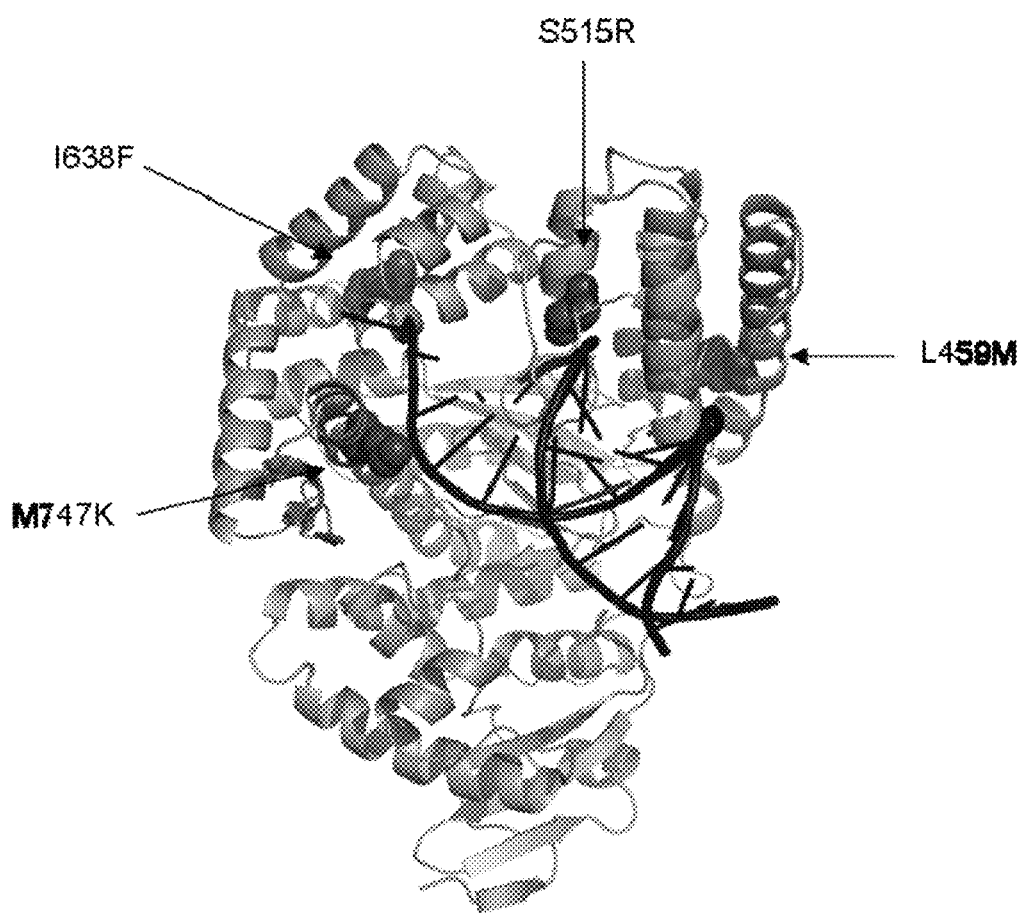

|  |  | Temp [°C] | Time [sec] | Repeat |
|---|---|---|---|---|
| Rev Transcription | Denaturation | 95 | 30 |  |
|  | Annealing | 55 | 35 |  |
|  | Extension | 72 | 7,5 min |  |
| PCR | Denaturation | 95 | 60 |  |
|  | Denaturation | 95 | 30 |  |
|  | Annealing | 55 | 35 | 49 |
|  | Extension | 72 | 40 |  |

B

|  |  | Temp [°C] | Time [sec] | Repeat |
|---|---|---|---|---|
| Rev Transcription | Denaturation | 95 | 30 |  |
|  | Annealing | 66 | 35 |  |
|  | Extension | 72 | 7,5 min |  |
| PCR | Denaturation | 95 | 60 |  |
|  | Denaturation | 95 | 30 |  |
|  | Annealing | 66 | 35 | 39 |
|  | Extension | 72 | 40 |  |

|  |  | Temp [°C] | Time [sec] | Repeat |
|---|---|---|---|---|
| Rev Transcription | Denaturation | 95 | 30 |  |
|  | Annealing | 55 | 35 |  |
|  | Extension | 72 | 7,5 min |  |
|  | Denaturation | 95 | 60 |  |
| PCR | Denaturation | 95 | 30 |  |
|  | Annealing | 55 | 35 | 49 |
|  | Extension | 72 | 40 |  |

SEQUENCE LISTING

```
<160> NUMBER OF SEQ ID NOS: 12

<210> SEQ ID NO 1
<211> LENGTH: 832
<212> TYPE: PRT
<213> ORGANISM: Thermus aquaticus

<400> SEQUENCE: 1

Met Arg Gly Met Leu Pro Leu Phe Glu Pro Lys Gly Arg Val Leu Leu
1               5                   10                  15
```

```
Val Asp Gly His His Leu Ala Tyr Arg Thr Phe His Ala Leu Lys Gly
         20                  25                  30

Leu Thr Thr Ser Arg Gly Glu Pro Val Gln Ala Val Tyr Gly Phe Ala
     35                  40                  45

Lys Ser Leu Leu Lys Ala Leu Lys Glu Asp Gly Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430
```

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
        450                 455                 460

Glu Glu Ile Ala Arg Leu Glu Ala Gly Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 2
<211> LENGTH: 540
<212> TYPE: PRT

<213> ORGANISM: Artificial Sequence
<220> FEATURE:
<223> OTHER INFORMATION: Chemically synthesized

<400> SEQUENCE: 2

```
Ala Leu Glu Glu Ala Pro Trp Pro Pro Glu Gly Ala Phe Val Gly
  1               5                  10                  15

Phe Val Leu Ser Arg Lys Glu Pro Met Trp Ala Asp Leu Leu Ala Leu
             20                  25                  30

Ala Ala Ala Arg Gly Gly Arg Val His Arg Ala Pro Glu Pro Tyr Lys
             35                  40                  45

Ala Leu Arg Asp Leu Lys Glu Ala Arg Gly Leu Leu Ala Lys Asp Leu
 50                  55                  60

Ser Val Leu Ala Leu Arg Glu Gly Leu Gly Leu Pro Pro Gly Asp Asp
 65                  70                  75                  80

Pro Met Leu Leu Ala Tyr Leu Leu Asp Pro Ser Asn Thr Thr Pro Glu
                 85                  90                  95

Gly Val Ala Arg Arg Tyr Gly Gly Glu Trp Thr Glu Glu Ala Gly Glu
                100                 105                 110

Arg Ala Ala Leu Ser Glu Arg Leu Phe Ala Asn Leu Trp Gly Arg Leu
            115                 120                 125

Glu Gly Glu Glu Arg Leu Leu Trp Leu Tyr Arg Glu Val Glu Arg Pro
130                 135                 140

Leu Ser Ala Val Leu Ala His Met Glu Ala Thr Gly Val Arg Leu Asp
145                 150                 155                 160

Val Ala Tyr Leu Arg Ala Leu Ser Leu Glu Val Ala Glu Glu Ile Ala
                165                 170                 175

Arg Leu Glu Ala Glu Val Phe Arg Leu Ala Gly His Pro Phe Asn Leu
            180                 185                 190

Asn Ser Arg Asp Gln Leu Glu Arg Val Leu Phe Asp Glu Leu Gly Leu
            195                 200                 205

Pro Ala Ile Gly Lys Thr Glu Lys Thr Gly Lys Arg Ser Thr Ser Ala
210                 215                 220

Ala Val Leu Glu Ala Leu Arg Glu Ala His Pro Ile Val Glu Lys Ile
225                 230                 235                 240

Leu Gln Tyr Arg Glu Leu Thr Lys Leu Lys Ser Thr Tyr Ile Asp Pro
                245                 250                 255

Leu Pro Asp Leu Ile His Pro Arg Thr Gly Arg Leu His Thr Arg Phe
            260                 265                 270

Asn Gln Thr Ala Thr Ala Thr Gly Arg Leu Ser Ser Ser Asp Pro Asn
            275                 280                 285

Leu Gln Asn Ile Pro Val Arg Thr Pro Leu Gly Gln Arg Ile Arg Arg
290                 295                 300

Ala Phe Ile Ala Glu Glu Gly Trp Leu Leu Val Ala Leu Asp Tyr Ser
305                 310                 315                 320

Gln Ile Glu Leu Arg Val Leu Ala His Leu Ser Gly Asp Glu Asn Leu
                325                 330                 335

Ile Arg Val Phe Gln Glu Gly Arg Asp Ile His Thr Glu Thr Ala Ser
            340                 345                 350

Trp Met Phe Gly Val Pro Arg Glu Ala Val Asp Pro Leu Met Arg Arg
            355                 360                 365

Ala Ala Lys Thr Ile Asn Phe Gly Val Leu Tyr Gly Met Ser Ala His
370                 375                 380

Arg Leu Ser Gln Glu Leu Ala Ile Pro Tyr Glu Glu Ala Gln Ala Phe
```

```
         385                 390                 395                 400
Ile Glu Arg Tyr Phe Gln Ser Phe Pro Lys Val Arg Ala Trp Ile Glu
                405                 410                 415

Lys Thr Leu Glu Glu Gly Arg Arg Gly Tyr Val Glu Thr Leu Phe
            420                 425                 430

Gly Arg Arg Tyr Val Pro Asp Leu Glu Ala Arg Val Lys Ser Val
        435                 440                 445

Arg Glu Ala Ala Glu Arg Met Ala Phe Asn Met Pro Val Gln Gly Thr
450                 455                 460

Ala Ala Asp Leu Met Lys Leu Ala Met Val Lys Leu Phe Pro Arg Leu
465                 470                 475                 480

Glu Glu Met Gly Ala Arg Met Leu Leu Gln Val His Asp Glu Leu Val
                485                 490                 495

Leu Glu Ala Pro Lys Glu Arg Ala Glu Val Ala Arg Leu Ala Lys
                500                 505                 510

Glu Val Met Glu Gly Val Tyr Pro Leu Ala Val Pro Leu Glu Val Glu
            515                 520                 525

Val Gly Ile Gly Glu Asp Trp Leu Ser Ala Lys Glu
    530                 535                 540

<210> SEQ ID NO 3
<211> LENGTH: 540
<212> TYPE: PRT
<213> ORGANISM: Artificial Sequence
<220> FEATURE:
<223> OTHER INFORMATION: Chemically synthesized

<400> SEQUENCE: 3

Ala Leu Glu Glu Ala Pro Trp Pro Pro Glu Gly Ala Phe Val Gly
1               5                   10                  15

Phe Val Leu Ser Arg Lys Glu Pro Met Trp Ala Asp Leu Leu Ala Leu
                20                  25                  30

Ala Ala Ala Arg Gly Gly Arg Val His Arg Ala Pro Glu Pro Tyr Lys
            35                  40                  45

Ala Leu Arg Asp Leu Lys Glu Ala Arg Gly Leu Leu Ala Lys Asp Leu
        50                  55                  60

Ser Val Leu Ala Leu Arg Glu Gly Leu Gly Leu Pro Pro Gly Asp Asp
65                  70                  75                  80

Pro Met Leu Leu Ala Tyr Leu Leu Asp Pro Ser Asn Thr Thr Pro Glu
                85                  90                  95

Gly Val Ala Arg Arg Tyr Gly Gly Glu Trp Thr Glu Glu Ala Gly Glu
            100                 105                 110

Arg Ala Ala Leu Ser Glu Arg Leu Phe Ala Asn Leu Trp Gly Arg Leu
        115                 120                 125

Glu Gly Glu Glu Arg Leu Leu Trp Leu Tyr Arg Glu Val Glu Arg Pro
130                 135                 140

Leu Ser Ala Val Leu Ala His Met Glu Ala Thr Gly Val Arg Leu Asp
145                 150                 155                 160

Val Ala Tyr Leu Arg Ala Leu Ser Leu Glu Val Ala Glu Glu Ile Ala
                165                 170                 175

Arg Leu Glu Ala Glu Val Phe Arg Leu Ala Gly His Pro Phe Asn Leu
            180                 185                 190

Asn Ser Arg Asp Gln Leu Glu Arg Val Leu Phe Asp Glu Leu Gly Leu
        195                 200                 205

Pro Ala Ile Gly Lys Thr Glu Lys Thr Gly Lys Arg Ser Thr Arg Ala
```

```
        210                 215                 220
Ala Val Leu Glu Ala Leu Arg Glu Ala His Pro Ile Val Glu Lys Ile
225                 230                 235                 240

Leu Gln Tyr Arg Glu Leu Thr Lys Leu Lys Ser Thr Tyr Ile Asp Pro
                245                 250                 255

Leu Pro Asp Leu Ile His Pro Arg Thr Gly Arg Leu His Thr Arg Phe
            260                 265                 270

Asn Gln Thr Ala Thr Ala Thr Gly Arg Leu Ser Ser Ser Asp Pro Asn
        275                 280                 285

Leu Gln Asn Ile Pro Val Arg Thr Pro Leu Gly Gln Arg Ile Arg Arg
    290                 295                 300

Ala Phe Ile Ala Glu Glu Gly Trp Leu Leu Val Ala Leu Asp Tyr Ser
305                 310                 315                 320

Gln Ile Glu Leu Arg Val Leu Ala His Leu Ser Gly Asp Glu Asn Leu
                325                 330                 335

Ile Arg Val Phe Gln Glu Gly Arg Asp Phe His Thr Glu Thr Ala Ser
            340                 345                 350

Trp Met Phe Gly Val Pro Arg Glu Ala Val Asp Pro Leu Met Arg Arg
        355                 360                 365

Ala Ala Lys Thr Ile Asn Phe Gly Val Leu Tyr Gly Met Ser Ala His
    370                 375                 380

Arg Leu Ser Gln Glu Leu Ala Ile Pro Tyr Glu Glu Ala Gln Ala Phe
385                 390                 395                 400

Ile Glu Arg Tyr Phe Gln Ser Phe Pro Lys Val Arg Ala Trp Ile Glu
                405                 410                 415

Lys Thr Leu Glu Glu Gly Arg Arg Gly Tyr Val Glu Thr Leu Phe
            420                 425                 430

Gly Arg Arg Arg Tyr Val Pro Asp Leu Glu Ala Arg Val Lys Ser Val
        435                 440                 445

Arg Glu Ala Ala Glu Arg Lys Ala Phe Asn Met Pro Val Gln Gly Thr
    450                 455                 460

Ala Ala Asp Leu Met Lys Leu Ala Met Val Lys Leu Phe Pro Arg Leu
465                 470                 475                 480

Glu Glu Met Gly Ala Arg Met Leu Leu Gln Val His Asp Glu Leu Val
                485                 490                 495

Leu Glu Ala Pro Lys Glu Arg Ala Glu Ala Val Ala Arg Leu Ala Lys
            500                 505                 510

Glu Val Met Glu Gly Val Tyr Pro Leu Ala Val Pro Leu Glu Val Glu
        515                 520                 525

Val Gly Ile Gly Glu Asp Trp Leu Ser Ala Lys Glu
    530                 535                 540

<210> SEQ ID NO 4
<211> LENGTH: 540
<212> TYPE: PRT
<213> ORGANISM: Artificial Sequence
<220> FEATURE:
<223> OTHER INFORMATION: Chemically synthesized

<400> SEQUENCE: 4

Ala Leu Glu Glu Ala Pro Trp Pro Pro Glu Gly Ala Phe Val Gly
1               5                   10                  15

Phe Val Leu Ser Arg Lys Glu Pro Met Trp Ala Asp Leu Leu Ala Leu
                20                  25                  30

Ala Ala Ala Arg Gly Gly Arg Val His Arg Ala Pro Glu Pro Tyr Lys
```

```
            35                  40                  45
Ala Leu Arg Asp Leu Lys Glu Ala Arg Gly Leu Leu Ala Lys Asp Leu
 50                  55                  60

Ser Val Leu Ala Leu Arg Glu Gly Leu Gly Leu Pro Pro Gly Asp Asp
 65                  70                  75                  80

Pro Met Leu Leu Ala Tyr Leu Leu Asp Pro Ser Asn Thr Thr Pro Glu
                     85                  90                  95

Gly Val Ala Arg Arg Tyr Gly Gly Glu Trp Thr Glu Ala Gly Glu
                100                 105                 110

Arg Ala Ala Leu Ser Glu Arg Leu Phe Ala Asn Leu Trp Gly Arg Leu
                115                 120                 125

Glu Gly Glu Glu Arg Leu Leu Trp Leu Tyr Arg Glu Val Glu Arg Pro
                130                 135                 140

Leu Ser Ala Val Leu Ala His Met Glu Ala Thr Gly Val Arg Leu Asp
145                 150                 155                 160

Val Ala Tyr Leu Arg Ala Met Ser Leu Glu Val Ala Glu Glu Ile Ala
                165                 170                 175

Arg Leu Glu Ala Glu Val Phe Arg Leu Ala Gly His Pro Phe Asn Leu
                180                 185                 190

Asn Ser Arg Asp Gln Leu Glu Arg Val Leu Phe Asp Glu Leu Gly Leu
                195                 200                 205

Pro Ala Ile Gly Lys Thr Glu Lys Thr Gly Lys Arg Ser Thr Arg Ala
                210                 215                 220

Ala Val Leu Glu Ala Leu Arg Glu Ala His Pro Ile Val Glu Lys Ile
225                 230                 235                 240

Leu Gln Tyr Arg Glu Leu Thr Lys Leu Lys Ser Thr Tyr Ile Asp Pro
                245                 250                 255

Leu Pro Asp Leu Ile His Pro Arg Thr Gly Arg Leu His Thr Arg Phe
                260                 265                 270

Asn Gln Thr Ala Thr Ala Thr Gly Arg Leu Ser Ser Ser Asp Pro Asn
                275                 280                 285

Leu Gln Asn Ile Pro Val Arg Thr Pro Leu Gly Gln Arg Ile Arg Arg
                290                 295                 300

Ala Phe Ile Ala Glu Glu Gly Trp Leu Leu Val Ala Leu Asp Tyr Ser
305                 310                 315                 320

Gln Ile Glu Leu Arg Val Leu Ala His Leu Ser Gly Asp Glu Asn Leu
                325                 330                 335

Ile Arg Val Phe Gln Glu Gly Arg Asp Phe His Thr Glu Thr Ala Ser
                340                 345                 350

Trp Met Phe Gly Val Pro Arg Glu Ala Val Asp Pro Leu Met Arg Arg
                355                 360                 365

Ala Ala Lys Thr Ile Asn Phe Gly Val Leu Tyr Gly Met Ser Ala His
                370                 375                 380

Arg Leu Ser Gln Glu Leu Ala Ile Pro Tyr Glu Glu Ala Gln Ala Phe
385                 390                 395                 400

Ile Glu Arg Tyr Phe Gln Ser Phe Pro Lys Val Arg Ala Trp Ile Glu
                405                 410                 415

Lys Thr Leu Glu Glu Gly Arg Arg Gly Tyr Val Glu Thr Leu Phe
                420                 425                 430

Gly Arg Arg Arg Tyr Val Pro Asp Leu Glu Ala Arg Val Lys Ser Val
                435                 440                 445

Arg Glu Ala Ala Glu Arg Lys Ala Phe Asn Met Pro Val Gln Gly Thr
                450                 455                 460
```

```
Ala Ala Asp Leu Met Lys Leu Ala Met Val Lys Leu Phe Pro Arg Leu
465                 470                 475                 480

Glu Glu Met Gly Ala Arg Met Leu Leu Gln Val His Asp Glu Leu Val
                485                 490                 495

Leu Glu Ala Pro Lys Glu Arg Ala Glu Ala Val Ala Arg Leu Ala Lys
            500                 505                 510

Glu Val Met Glu Gly Val Tyr Pro Leu Ala Val Pro Leu Glu Val Glu
        515                 520                 525

Val Gly Ile Gly Glu Asp Trp Leu Ser Ala Lys Glu
530                 535                 540

<210> SEQ ID NO 5
<211> LENGTH: 540
<212> TYPE: PRT
<213> ORGANISM: Artificial Sequence
<220> FEATURE:
<223> OTHER INFORMATION: Chemically synthesized

<400> SEQUENCE: 5

Ala Leu Glu Glu Ala Pro Trp Pro Pro Glu Gly Ala Phe Val Gly
1               5                   10                  15

Phe Val Leu Ser Arg Lys Glu Pro Met Trp Ala Asp Leu Met Ala Leu
                20                  25                  30

Ala Ala Ala Arg Gly Gly Arg Val His Arg Ala Pro Glu Pro Tyr Lys
                35                  40                  45

Ala Leu Arg Asp Leu Lys Glu Ala Arg Gly Leu Leu Ala Lys Asp Leu
            50                  55                  60

Ser Val Leu Ala Leu Arg Glu Gly Leu Gly Leu Pro Pro Gly Asp Asp
65                  70                  75                  80

Pro Met Leu Leu Ala Tyr Leu Leu Asp Pro Ser Asn Thr Thr Pro Glu
                85                  90                  95

Gly Val Ala Arg Arg Tyr Gly Gly Glu Trp Thr Glu Glu Ala Gly Glu
                100                 105                 110

Arg Ala Ala Leu Ser Glu Arg Leu Phe Ala Asn Leu Trp Gly Arg Leu
                115                 120                 125

Glu Gly Glu Glu Arg Leu Leu Trp Leu Tyr Arg Glu Val Glu Arg Pro
                130                 135                 140

Leu Ser Ala Val Leu Ala His Met Glu Ala Thr Gly Val Arg Leu Asp
145                 150                 155                 160

Val Ala Tyr Leu Arg Ala Met Ser Leu Glu Val Ala Glu Glu Ile Ala
                165                 170                 175

Arg Leu Glu Ala Glu Val Phe Arg Leu Ala Gly His Pro Phe Asn Leu
                180                 185                 190

Asn Ser Arg Asp Gln Leu Glu Arg Val Leu Phe Asp Glu Leu Gly Leu
                195                 200                 205

Pro Ala Ile Gly Lys Thr Glu Lys Thr Gly Lys Arg Ser Thr Arg Ala
                210                 215                 220

Ala Val Leu Glu Ala Leu Arg Glu Ala His Pro Ile Val Glu Lys Ile
225                 230                 235                 240

Leu Gln Tyr Arg Glu Leu Thr Lys Leu Lys Ser Thr Tyr Ile Asp Pro
                245                 250                 255

Leu Pro Asp Leu Ile His Pro Arg Thr Gly Arg Leu His Thr Arg Phe
                260                 265                 270

Asn Gln Thr Ala Thr Ala Thr Gly Arg Leu Ser Ser Ser Asp Pro Asn
                275                 280                 285
```

Leu Gln Asn Ile Pro Val Arg Thr Pro Leu Gly Gln Arg Ile Arg Arg
            290                 295                 300

Ala Phe Ile Ala Glu Glu Gly Trp Leu Leu Val Ala Leu Asp Tyr Ser
305                 310                 315                 320

Gln Ile Glu Leu Arg Val Leu Ala His Leu Ser Gly Asp Glu Asn Leu
                325                 330                 335

Ile Arg Val Phe Gln Glu Gly Arg Asp Phe His Thr Glu Thr Ala Ser
            340                 345                 350

Trp Met Phe Gly Val Pro Arg Glu Ala Val Asp Pro Leu Met Arg Arg
        355                 360                 365

Ala Ala Lys Thr Ile Asn Phe Gly Val Leu Tyr Gly Met Ser Ala His
    370                 375                 380

Arg Leu Ser Gln Glu Leu Ala Ile Pro Tyr Glu Glu Ala Gln Ala Phe
385                 390                 395                 400

Ile Glu Arg Tyr Phe Gln Ser Phe Pro Lys Val Arg Ala Trp Ile Glu
                405                 410                 415

Lys Thr Leu Glu Glu Gly Arg Arg Gly Tyr Val Glu Thr Leu Phe
            420                 425                 430

Gly Arg Arg Arg Tyr Val Pro Asp Leu Glu Ala Arg Val Lys Ser Val
        435                 440                 445

Arg Glu Ala Ala Glu Arg Lys Ala Phe Asn Met Pro Val Gln Gly Thr
450                 455                 460

Ala Ala Asp Leu Met Lys Leu Ala Met Val Lys Leu Phe Pro Arg Leu
465                 470                 475                 480

Glu Glu Met Gly Ala Arg Met Leu Leu Gln Val His Asp Glu Leu Val
                485                 490                 495

Leu Glu Ala Pro Lys Glu Arg Ala Glu Ala Val Ala Arg Leu Ala Lys
            500                 505                 510

Glu Val Met Glu Gly Val Tyr Pro Leu Ala Val Pro Leu Glu Val Glu
        515                 520                 525

Val Gly Ile Gly Glu Asp Trp Leu Ser Ala Lys Glu
    530                 535                 540

<210> SEQ ID NO 6
<211> LENGTH: 540
<212> TYPE: PRT
<213> ORGANISM: Artificial Sequence
<220> FEATURE:
<223> OTHER INFORMATION: Chemically synthesized

<400> SEQUENCE: 6

Ala Leu Glu Glu Ala Pro Trp Pro Pro Glu Gly Ala Phe Val Gly
1               5                   10                  15

Phe Val Leu Ser Arg Lys Glu Pro Met Trp Ala Asp Leu Met Ala Leu
                20                  25                  30

Ala Ala Ala Arg Gly Gly Arg Val His Arg Ala Pro Glu Pro Tyr Lys
            35                  40                  45

Ala Leu Arg Asp Leu Lys Glu Ala Arg Gly Leu Leu Ala Lys Asp Leu
        50                  55                  60

Ser Val Leu Ala Leu Arg Glu Gly Leu Gly Leu Pro Pro Gly Asp Asp
65                  70                  75                  80

Pro Met Leu Leu Ala Tyr Leu Leu Asp Pro Ser Asn Thr Thr Pro Glu
                85                  90                  95

Gly Val Ala Arg Arg Tyr Gly Gly Glu Trp Thr Glu Glu Ala Gly Glu
            100                 105                 110

```
Arg Ala Ala Leu Ser Glu Arg Leu Phe Ala Asn Leu Trp Gly Arg Leu
        115                 120                 125

Glu Gly Glu Glu Arg Leu Leu Trp Leu Tyr Arg Gly Val Glu Arg Pro
130                 135                 140

Leu Ser Ala Val Leu Ala His Met Glu Ala Thr Gly Val Arg Leu Asp
145                 150                 155                 160

Val Ala Tyr Leu Arg Ala Met Ser Leu Glu Val Ala Glu Glu Ile Ala
                165                 170                 175

Arg Leu Glu Ala Glu Val Phe Arg Leu Ala Gly His Pro Phe Asn Leu
                180                 185                 190

Asn Ser Arg Asp Gln Leu Glu Arg Val Leu Phe Asp Glu Leu Gly Leu
        195                 200                 205

Pro Ala Ile Gly Lys Thr Glu Lys Thr Gly Lys Arg Ser Thr Arg Ala
        210                 215                 220

Ala Val Leu Glu Ala Leu Arg Glu Ala His Pro Ile Val Glu Lys Ile
225                 230                 235                 240

Leu Gln Tyr Arg Glu Leu Thr Lys Leu Lys Ser Thr Tyr Ile Asp Pro
                245                 250                 255

Leu Pro Asp Leu Ile His Pro Arg Thr Gly Arg Leu His Thr Arg Phe
                260                 265                 270

Asn Gln Thr Ala Thr Ala Thr Gly Arg Leu Ser Ser Ser Asp Pro Asn
        275                 280                 285

Leu Gln Asn Ile Pro Val Arg Thr Pro Leu Gly Gln Arg Ile Arg Arg
        290                 295                 300

Ala Phe Ile Ala Glu Glu Gly Trp Leu Leu Val Ala Leu Asp Tyr Ser
305                 310                 315                 320

Gln Ile Glu Leu Arg Val Leu Ala His Leu Ser Gly Asp Glu Asn Leu
                325                 330                 335

Ile Arg Val Phe Gln Glu Gly Arg Asp Phe His Thr Glu Thr Ala Ser
                340                 345                 350

Trp Met Phe Gly Val Pro Arg Glu Ala Val Asp Pro Leu Met Arg Arg
        355                 360                 365

Ala Ala Lys Thr Ile Asn Phe Gly Val Leu Tyr Gly Met Ser Ala His
        370                 375                 380

Arg Leu Ser Gln Glu Leu Ala Ile Pro Tyr Glu Glu Ala Gln Ala Phe
385                 390                 395                 400

Ile Glu Arg Tyr Phe Gln Ser Phe Pro Lys Val Arg Ala Trp Ile Glu
                405                 410                 415

Lys Thr Leu Glu Glu Gly Arg Arg Gly Tyr Val Glu Thr Leu Phe
                420                 425                 430

Gly Arg Arg Arg Tyr Val Pro Asp Leu Glu Ala Arg Val Lys Ser Val
        435                 440                 445

Arg Glu Ala Ala Glu Arg Lys Ala Phe Asn Met Pro Val Gln Gly Thr
450                 455                 460

Ala Ala Asp Leu Met Lys Leu Ala Met Val Lys Leu Phe Pro Arg Leu
465                 470                 475                 480

Gly Glu Met Gly Ala Arg Met Leu Leu Gln Val His Asp Glu Leu Val
                485                 490                 495

Leu Glu Ala Pro Lys Glu Arg Ala Glu Ala Val Ala Arg Leu Ala Lys
                500                 505                 510

Glu Val Met Glu Gly Val Tyr Pro Leu Ala Val Pro Leu Glu Val Glu
        515                 520                 525
```

Val Gly Ile Gly Glu Asp Trp Leu Ser Ala Lys Glu
            530                 535                 540

<210> SEQ ID NO 7
<211> LENGTH: 540
<212> TYPE: PRT
<213> ORGANISM: Artificial Sequence
<220> FEATURE:
<223> OTHER INFORMATION: Chemically synthesized

<400> SEQUENCE: 7

Ala Leu Glu Glu Ala Pro Trp Pro Pro Glu Gly Ala Phe Val Gly
1               5                   10                  15

Phe Val Leu Ser Arg Lys Glu Pro Met Trp Ala Asp Leu Met Ala Leu
            20                  25                  30

Ala Ala Ala Arg Gly Gly Arg Val His Arg Ala Pro Glu Pro Tyr Lys
        35                  40                  45

Ala Leu Arg Asp Leu Lys Glu Ala Arg Gly Leu Leu Ala Lys Asp Leu
    50                  55                  60

Ser Val Leu Ala Leu Arg Glu Gly Leu Gly Leu Pro Pro Gly Asp Asp
65                  70                  75                  80

Pro Met Leu Leu Ala Tyr Leu Leu Asp Pro Ser Asn Thr Thr Pro Glu
                85                  90                  95

Gly Val Ala Arg Arg Tyr Gly Gly Glu Trp Thr Glu Glu Ala Gly Glu
            100                 105                 110

Arg Ala Ala Leu Ser Glu Arg Leu Phe Ala Asn Leu Trp Gly Arg Leu
        115                 120                 125

Glu Gly Glu Glu Arg Leu Leu Trp Leu Tyr Arg Glu Val Glu Arg Pro
    130                 135                 140

Leu Ser Ala Val Leu Ala His Met Glu Ala Thr Gly Val Arg Leu Asp
145                 150                 155                 160

Val Ala Tyr Leu Arg Ala Met Ser Leu Glu Val Ala Glu Glu Ile Ala
                165                 170                 175

Arg Leu Glu Ala Glu Val Phe Arg Leu Ala Gly His Pro Phe Asn Leu
            180                 185                 190

Asn Ser Arg Asp Gln Leu Glu Arg Val Leu Phe Asp Glu Leu Gly Leu
        195                 200                 205

Pro Ala Ile Gly Lys Thr Glu Lys Thr Gly Lys Arg Ser Thr Arg Ala
    210                 215                 220

Ala Val Leu Glu Ala Leu Arg Glu Ala His Pro Ile Val Glu Lys Ile
225                 230                 235                 240

Leu Gln Tyr Arg Glu Leu Thr Lys Leu Lys Ser Thr Tyr Ile Asp Pro
                245                 250                 255

Leu Pro Asp Leu Ile His Pro Arg Thr Gly Arg Leu His Thr Arg Phe
            260                 265                 270

Asn Gln Thr Ala Thr Ala Thr Gly Arg Leu Ser Ser Ser Asp Pro Asn
        275                 280                 285

Leu Gln Asn Ile Pro Val Arg Thr Pro Leu Gly Gln Arg Ile Arg Arg
    290                 295                 300

Ala Phe Ile Ala Glu Glu Gly Trp Leu Leu Val Ala Leu Asp Tyr Ser
305                 310                 315                 320

Gln Ile Glu Leu Arg Val Leu Ala His Leu Ser Gly Asp Glu Asn Leu
                325                 330                 335

Ile Arg Val Phe Gln Glu Gly Arg Asp Phe His Thr Glu Thr Ala Ser
            340                 345                 350

Trp Met Phe Gly Val Pro Arg Glu Ala Val Asp Pro Leu Met Arg Arg
            355                 360                 365

Ala Ala Lys Thr Ile Asn Phe Gly Val Leu Tyr Gly Met Ser Ala His
    370                 375                 380

Arg Leu Ser Gln Glu Leu Ala Ile Pro Tyr Glu Glu Ala Gln Ala Phe
385                 390                 395                 400

Ile Glu Arg Tyr Phe Gln Ser Phe Pro Lys Val Arg Ala Trp Ile Glu
                405                 410                 415

Lys Thr Leu Glu Glu Gly Arg Arg Gly Tyr Val Glu Thr Leu Phe
            420                 425                 430

Gly Arg Arg Arg Tyr Val Pro Asp Leu Glu Ala Arg Val Lys Gly Val
        435                 440                 445

Arg Glu Ala Ala Glu Arg Lys Ala Phe Asn Met Pro Val Gln Gly Thr
    450                 455                 460

Ala Ala Asp Leu Met Lys Leu Ala Met Val Lys Leu Phe Pro Arg Leu
465                 470                 475                 480

Gly Glu Met Gly Ala Arg Met Leu Leu Gln Val His Asp Glu Leu Val
                485                 490                 495

Leu Glu Ala Pro Lys Glu Arg Ala Glu Ala Val Ala Arg Leu Ala Lys
            500                 505                 510

Glu Val Met Glu Gly Val Tyr Pro Leu Ala Val Pro Leu Glu Val Glu
        515                 520                 525

Val Gly Ile Gly Glu Asp Trp Leu Ser Ala Lys Glu
    530                 535                 540

<210> SEQ ID NO 8
<211> LENGTH: 832
<212> TYPE: PRT
<213> ORGANISM: Artificial Sequence
<220> FEATURE:
<223> OTHER INFORMATION: Chemically synthesized

<400> SEQUENCE: 8

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

```
Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
        210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
        500                 505                 510

Ser Thr Arg Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
```

```
                    595                 600                 605
Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Phe His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Lys Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 9
<211> LENGTH: 832
<212> TYPE: PRT
<213> ORGANISM: Artificial Sequence
<220> FEATURE:
<223> OTHER INFORMATION: Chemically synthesized

<400> SEQUENCE: 9

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
```

```
              130                 135                 140
Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
                195                 200                 205

Glu Glu Trp Gly Ser Leu Glu Ala Leu Leu Lys Asn Leu Asp Arg Leu
        210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Met Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Arg Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560
```

-continued

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
        580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
610                 615                 620

Asp Glu Asn Leu Ile Arg Val Phe Gln Glu Gly Arg Asp Phe His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
        660                 665                 670

Met Ser Ala His Arg Leu Ser Gln Glu Leu Ala Ile Pro Tyr Glu Glu
    675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Lys Ala Phe Asn Met Pro
        740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
        820                 825                 830

<210> SEQ ID NO 10
<211> LENGTH: 832
<212> TYPE: PRT
<213> ORGANISM: Artificial Sequence
<220> FEATURE:
<223> OTHER INFORMATION: Chemically synthesized

<400> SEQUENCE: 10

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
            85                  90                  95

```
Ala Leu Ile Lys Glu Leu Val Asp Leu Leu Gly Leu Ala Arg Leu Glu
            100                 105                 110

Val Pro Gly Tyr Glu Ala Asp Val Leu Ala Ser Leu Ala Lys Lys
            115                 120                 125

Ala Glu Lys Glu Gly Tyr Glu Val Arg Ile Leu Thr Ala Asp Lys Asp
        130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Met Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Met Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510
```

Ser Thr Arg Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Phe His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Lys Ala Phe Asn Met Pro
            740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 11
<211> LENGTH: 832
<212> TYPE: PRT
<213> ORGANISM: Artificial Sequence
<220> FEATURE:
<223> OTHER INFORMATION: Chemically synthesized

<400> SEQUENCE: 11

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

```
Lys Ser Leu Leu Lys Ala Leu Lys Glu Asp Gly Asp Ala Val Ile Val
    50                  55                  60
Val Phe Asp Ala Lys Ala Pro Ser Phe Arg His Glu Ala Tyr Gly Gly
 65                  70                  75                  80
Tyr Lys Ala Gly Arg Ala Pro Thr Pro Glu Asp Phe Pro Arg Gln Leu
                 85                  90                  95
Ala Leu Ile Lys Glu Leu Val Asp Leu Leu Gly Leu Ala Arg Leu Glu
                100                 105                 110
Val Pro Gly Tyr Glu Ala Asp Asp Val Leu Ala Ser Leu Ala Lys Lys
                115                 120                 125
Ala Glu Lys Glu Gly Tyr Glu Val Arg Ile Leu Thr Ala Asp Lys Asp
    130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
                180                 185                 190
Leu Pro Gly Val Lys Gly Ile Gly Glu Lys Thr Ala Arg Lys Leu Leu
                195                 200                 205
Glu Glu Trp Gly Ser Leu Glu Ala Leu Leu Lys Asn Leu Asp Arg Leu
    210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
    275                 280                 285
Glu Ser Pro Lys Ala Leu Glu Glu Ala Pro Trp Pro Pro Pro Glu Gly
    290                 295                 300
Ala Phe Val Gly Phe Val Leu Ser Arg Lys Glu Pro Met Trp Ala Asp
305                 310                 315                 320
Leu Met Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
    355                 360                 365
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Met Ser Leu Glu Val Ala
    450                 455                 460
Glu Glu Ile Ala Arg Leu Glu Ala Glu Val Phe Arg Leu Ala Gly His
```

```
            465                 470                 475                 480

Pro Phe Asn Leu Asn Ser Arg Asp Gln Leu Glu Arg Val Leu Phe Asp
                    485                 490                 495

Glu Leu Gly Leu Pro Ala Ile Gly Lys Thr Glu Lys Thr Gly Lys Arg
                500                 505                 510

Ser Thr Arg Ala Ala Val Leu Glu Ala Leu Arg Glu Ala His Pro Ile
                515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
    545                 550                 555                 560

His Thr Arg Phe Asn Gln Thr Ala Thr Ala Thr Gly Arg Leu Ser Ser
                    565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Phe His Thr
    625                 630                 635                 640

Glu Thr Ala Ser Trp Met Phe Gly Val Pro Arg Glu Ala Val Asp Pro
                    645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
                675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
    705                 710                 715                 720

Glu Thr Leu Phe Gly Arg Arg Arg Tyr Val Pro Asp Leu Glu Ala Arg
                    725                 730                 735

Val Lys Ser Val Arg Glu Ala Ala Glu Arg Lys Ala Phe Asn Met Pro
                740                 745                 750

Val Gln Gly Thr Ala Ala Asp Leu Met Lys Leu Ala Met Val Lys Leu
                755                 760                 765

Phe Pro Arg Leu Gly Glu Met Gly Ala Arg Met Leu Leu Gln Val His
        770                 775                 780

Asp Glu Leu Val Leu Glu Ala Pro Lys Glu Arg Ala Glu Ala Val Ala
    785                 790                 795                 800

Arg Leu Ala Lys Glu Val Met Glu Gly Val Tyr Pro Leu Ala Val Pro
                    805                 810                 815

Leu Glu Val Glu Val Gly Ile Gly Glu Asp Trp Leu Ser Ala Lys Glu
                820                 825                 830

<210> SEQ ID NO 12
<211> LENGTH: 832
<212> TYPE: PRT
<213> ORGANISM: Artificial Sequence
<220> FEATURE:
<223> OTHER INFORMATION: Chemically synthesized

<400> SEQUENCE: 12

Met Arg Gly Met Leu Pro Leu Phe Glu Pro Lys Gly Arg Val Leu Leu
```

-continued

```
1               5                   10                  15
Val Asp Gly His His Leu Ala Tyr Arg Thr Phe His Ala Leu Lys Gly
            20                  25                  30
Leu Thr Thr Ser Arg Gly Glu Pro Val Gln Ala Val Tyr Gly Phe Ala
            35                  40                  45
Lys Ser Leu Leu Lys Ala Leu Lys Glu Asp Gly Asp Ala Val Ile Val
            50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
            85                  90                  95
Ala Leu Ile Lys Glu Leu Val Asp Leu Leu Gly Leu Ala Arg Leu Glu
            100                 105                 110
Val Pro Gly Tyr Glu Ala Asp Asp Val Leu Ala Ser Leu Ala Lys Lys
            115                 120                 125
Ala Glu Lys Glu Gly Tyr Glu Val Arg Ile Leu Thr Ala Asp Lys Asp
            130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
            165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
            195                 200                 205
Glu Glu Trp Gly Ser Leu Glu Ala Leu Leu Lys Asn Leu Asp Arg Leu
            210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
            245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
            275                 280                 285
Glu Ser Pro Lys Ala Leu Glu Glu Ala Pro Trp Pro Pro Pro Glu Gly
            290                 295                 300
Ala Phe Val Gly Phe Val Leu Ser Arg Lys Glu Pro Met Trp Ala Asp
305                 310                 315                 320
Leu Met Ala Leu Ala Ala Ala Arg Gly Gly Arg Val His Arg Ala Pro
            325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
            405                 410                 415
Trp Gly Arg Leu Glu Gly Glu Glu Arg Leu Leu Trp Leu Tyr Arg Glu
            420                 425                 430
```

```
Val Glu Arg Pro Leu Ser Ala Val Leu Ala His Met Glu Ala Thr Gly
        435                 440                 445
Val Arg Leu Asp Val Ala Tyr Leu Arg Ala Met Ser Leu Glu Val Ala
    450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Arg Ala Ala Val Leu Glu Ala Leu Arg Glu Ala His Pro Ile
        515                 520                 525
Val Glu Lys Ile Leu Gln Tyr Arg Glu Leu Thr Lys Leu Lys Ser Thr
    530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
        595                 600                 605
Leu Asp Tyr Ser Gln Ile Glu Leu Arg Val Leu Ala His Leu Ser Gly
    610                 615                 620
Asp Glu Asn Leu Ile Arg Val Phe Gln Glu Gly Arg Asp Phe His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
        675                 680                 685
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Gly Val Arg Glu Ala Ala Glu Arg Lys Ala Phe Asn Met Pro
            740                 745                 750
Val Gln Gly Thr Ala Ala Asp Leu Met Lys Leu Ala Met Val Lys Leu
        755                 760                 765
Phe Pro Arg Leu Gly Glu Met Gly Ala Arg Met Leu Leu Gln Val His
    770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
            820                 825                 830
```

DNA POLYMERASES WITH INCREASED SUBSTRATE SCOPE

CROSS-REFERENCE TO RELATED APPLICATIONS

This application is the U.S. national phase application filed under 35 U.S.C. §371 claiming benefit to International Patent Application No. PCT/EP12/003388, filed on Aug. 8, 2012, the disclosure of which is incorporated herein by reference in their entirety.

The present invention relates to DNA polymerases displaying increased substrate scope such as improved reverse transcriptase and DNA polymerase activities, as well as improved activities for incorporating and extending modified nucleotides. In particular, the present invention relates to DNA polymerases derived from wild-type *Thermus aquaticus* (Taq) polymerase, comprising the mutations S515R, I638F, and M747K with regard to the wild-type amino acid sequence. The present invention further relates to nucleic acids coding for the DNA polymerases of the present invention, vectors containing said nucleic acids, host cells containing said vectors or nucleic acids, methods for the generation of DNA molecules using said DNA polymerases, kits containing said DNA polymerases, and uses thereof.

A widespread and well established technique for the detection of RNA molecules is the so-called reverse transcription polymerase chain reaction (RT-PCR). In RT-PCR, RNA is reverse transcribed into its DNA complement (complementary DNA, or cDNA), and then the resulting cDNA is amplified using PCR. RT-PCR provides a highly sensitive technique for the detection of RNA molecules even at low or very low copy numbers. It is used for example in the diagnosis of genetic diseases, the determination of the abundance of specific RNA molecules in a cell or tissue, or the study of RNA viruses such as Influenzavirus A or human immunodeficiency virus (HIV).

Another important use of RT-PCR techniques is the detection of unwanted microorganisms, e.g. food-borne microorganisms. Infections with food-borne pathogens belong to the most serious public health hazards today. With the increase of worldwide travel and trade, the risk of spreading dangerous pathogens has grown consistently. As a counter-measure, microbiological quality control procedures in the production and processing of foods are becoming increasingly important. Accordingly, the development of faster, more robust, more reliable and more selective methods for the detection and characterization of microorganisms is of paramount interest and importance.

Conventional methods for the detection of microorganisms include for example the cultivation of suspicious colonies or samples followed by biochemical and/or serological identification of the respective microorganisms. As these methods display several important drawbacks, such as a lack of sensitivity and the inability to detect certain microorganisms at all, the detection of specific genomic sequences of microorganisms by PCR, which allows the detection of very small amounts of microorganisms, has found widespread use. However, respective methods still have several drawbacks. As an example, a lack of specificity often prohibits the detection of bacterial DNA on a background of non-bacterial DNA such as host cell DNA. Moreover, such methods do not allow for the discrimination of live and dead microorganisms. Therefore, RT-PCR for the detection of specific mRNA molecules, which are present only in live microorganisms, is emerging as an attractive alternative for the detection of microorganisms. However, RT-PCR techniques still often lack the desired selectivity and sensitivity, leaving room for improvements and a need for further development.

Most RT-PCR techniques known in the art are based on the use of two different enzymes, i.e. a reverse transcriptase for reverse transcription of RNA into cDNA, and a DNA polymerase for the subsequent amplification of said cDNA. These techniques often require sample manipulations between reverse transcription and amplification, such as RNA digestion after reverse transcription or the addition of different buffers. These sample manipulations are not only time- and labor-intensive, but also pose the risk of sample contamination.

Unfortunately, reverse transcriptases are often not as thermostable as DNA polymerases, limiting their application temperature range. Therefore, reverse transcriptases known in the art can be often not used at elevated temperatures to synthesize first-strand cDNA. Thus, cDNA synthesis from RNA with secondary structures can be markedly inhibited. The use of a DNA polymerase derived from *Thermus thermophilus* (Tth polymerase) which has a reverse transcriptase activity in addition to its DNA polymerase activity, eliminates the need for two different enzymes and offers the possibility for reverse transcription at elevated temperatures. However, Tth polymerase requires the presence of $Mn^{2+}$ ions for reverse transcription. Nevertheless, the presence of said ions during DNA amplification is not desirable. Thus, respective techniques still require a step of sample manipulation between reverse transcription and DNA amplification, e.g. the addition of a chelating agent such as EDTA. Thus, one-enzyme RT-PCR techniques still require sample manipulations between reverse transcription and amplification, which limits their use in high-throughput formats and constitutes an additional source of sample contamination.

Further enzymes having both reverse transcriptase and DNA polymerase activities for use in RT-PCR techniques have been developed. These include enzymes derived from Taq polymerase, such as the M1 polymerase having the mutations L322M, L459M, S515R, I638F, S739G, and E773G with regard to wild-type Taq polymerase. However, this polymerase still leaves room for further improvements, e.g. concerning its enzymatic activities and thermostability.

Therefore, there is a need for improved enzymes having the ability to accept RNA as a template, and having increased reverse transcriptase and DNA polymerase activities. Respective enzymes should further display an improved thermostability within the temperature range used in PCR, which would further allow for the detection of RNA molecules having strong secondary structures which can only be eliminated at high temperatures.

Numerous 2'-deoxynucleoside triphosphates (dNTPs) that are functionalized with spacious modifications such as dyes or affinity tags are substrates for DNA polymerases. The capability of DNA polymerases to accept such modified dNTPs and templates is exploited in many important biotechnological applications including next-generation sequencing approaches, single molecule sequencing, labeling of DNA and PCR amplificates, e.g. for microarray analysis, DNA conjugation, or the in vitro selection of ligands such as aptamers by SELEX (systematic enrichment of ligands by exponential amplification). Furthermore, utilizing the intrinsic properties of DNA in combination with chemically introduced functionalities provides an entry to new classes of nucleic acids-based hybrid materials. Nevertheless, DNA polymerases known in the art still require further optimization to show increased activities for incorporating the growing number of known and still to be established modified nucleotides into DNA.

Of interest, KlenTaq M747K polymerase was reported having the mutation M747K with regard to wild-type Taq polymerase that has higher propensity to bypass DNA lesions.

Accordingly, the technical problem underlying the present invention is to provide novel enzymes having the above advantageous characteristics.

The solution to the above technical problem is achieved by the embodiments characterized in the claims.

In particular, in a first aspect, the present invention relates to a DNA polymerase derived from wild-type *Thermus aquaticus* (Taq) DNA polymerase, comprising at least one of the mutations S515R, I638F, and M747K with regard to the amino acid sequence of wild-type Taq DNA polymerase (SEQ ID NO: 1).

In a particularly preferred embodiment of the DNA polymerase of the present invention, said DNA polymerase comprises all three of the mutations S515R, I638F, and M747K with regard to the amino acid sequence of wild-type Taq DNA polymerase (SEQ ID NO: 1). This DNA polymerase is sometimes referred to as "C12 DNA polymerase" hereinafter.

The term "DNA polymerase" as used herein includes DNA polymerases that have been modified by e.g. natural process such as posttranslational processing, or non-natural process such as chemical modification. Such modifications can occur on the peptide backbone, amino acid side chains, or the N- or C-terminus. Modifications include e.g. acetylations, acylations, ADP-ribosylations, amidations, covalent attachment of flavines, haem-groups, nucleotides or nucleotide derivatives, lipids or lipid derivatives, cyclizations, disulfide bridges, methylations and demethylations, cystine linkages, formylations, γ-carboxylations, glycosylations, hydroxylations, phosphorylations and the tRNA-mediated addition of amino acids.

The expression "derived from wild-type Taq polymerase" as used herein relates to the fact that the DNA polymerase of the present invention is substantially identical to wild-type Taq polymerase, provided at least one of the above mutations is present. However, said expression also includes DNA polymerases whose amino acid sequence has one or more further amino acid substitutions, deletions or additions as compared to the amino acid sequence of wild-type Taq polymerase, provided at least one of the above mutations is present and provided the DNA polymerase retains its reverse transcriptase and DNA polymerase activities. In particular, the DNA polymerase of the present invention can comprise an amino acid sequence that has more than 70%, more than 80%, more than 85%, more than 90%, more than 92%, more than 94%, more than 96%, more than 97%, more than 98%, or more than 99% identify to SEQ ID NO: 1, provided at least one of the above mutations is present. In a particular embodiment, the DNA polymerase of the present invention comprises the amino acid sequence as shown in SEQ ID NO: 1 including at least one of the above mutations. In another embodiment, the DNA polymerase of the present invention comprises the amino acid sequence corresponding to amino acids 293 to 832 of SEQ ID NO: 1 including at least one of the above mutations. In a further embodiment, the DNA polymerase of the present invention comprises the amino acid sequence as shown in SEQ ID NO: 2, known as KlenTaq DNA polymerase, including at least one of the above mutations. In this context, amino acids 1 to 540 of SEQ ID NO: 2 correspond to amino acids 293 to 832 of SEQ ID NO: 1, i.e. KlenTaq DNA polymerase is a C-terminal fragment of Taq polymerase.

The expression "including said mutations" as used herein refers to the fact that at least one of the above mutations, i.e. of the mutations S515R, I638F, and M747K with regard to the amino acid sequence of wild-type Taq DNA polymerase (SEQ ID NO: 1), is present in any case. As an example, the expression "comprising the amino acid sequence as shown in SEQ ID NO: 1 including at least one of said mutations" as used herein refers to a DNA polymerase comprising the amino acid sequence as shown in SEQ ID NO 1, with the exception that in comparison to the amino acid sequence shown in SEQ ID NO: 1, the amino acid sequence of the DNA polymerase of the present invention comprises at least one of an arginine (R) in position 515 instead of a serine (S), a phenylalanine (F) in position 638 instead of an isoleucine (I), and/or a lysine (K) in position 747 instead of a methionine (M).

The notation of mutations as used herein is a standard notation known in the art. As an example, the mutation S515R is a mutation at position 515, where a serine (S) has been exchanged for an arginine (R).

The expression "with regard to SEQ ID NO: 1" as used herein refers to the fact that all mutations mentioned in the present application are to be seen in relation to the wild-type sequence of Taq polymerase provided in SEQ ID NO: 1. As an example, a DNA polymerase according to the present invention can have the amino acid sequence shown in SEQ ID NO: 2 including the mutations S515R, I638F, and M747K with regard to SEQ ID NO: 1. These mutations are actually in positions 223, 346, and 455 of the actual amino acid sequence of the DNA polymerase. However, said mutations are nevertheless labeled S515R, I638F, and M747K, since all mutations are to be seen with regard to SEQ ID NO: 1.

In preferred embodiments, the DNA polymerase of the present invention comprises all three of the mutations S515R, I638F, and M747K with regard to SEQ ID NO: 1 and one or more further mutations, selected from the group consisting of L322M, L459M, S739G, E773G, and L789F with regard to SEQ ID NO: 1. Particular embodiments of the DNA polymerase of the present invention include DNA polymerases having the above mutations S515R, I638F, and M747K with regard to SEQ ID NO: 1 (C12 DNA polymerase), and further comprising (i) the mutation L459M with regard to SEQ ID NO: 1 (D9 DNA polymerase), (ii) the mutations L322M and L459M with regard to SEQ ID NO: 1 (F4 DNA polymerase), (iii) the mutations L322M, L459M, and E773G with regard to SEQ ID NO: 1 (E9 DNA polymerase), or (iv) the mutations L322M, L459M, S739G, and E773G with regard to SEQ ID NO: 1 (M1/M747K DNA polymerase). Hereinafter, the DNA polymerases are designated either as e.g. "D9 DNA polymerase", or, when derived from the full-length Taq DNA polymerase as "Taq D9", or, when derived from the KlenTaq fragment of Taq DNA polymerase, as "KlenTaq D9".

In particularly preferred embodiments, the DNA polymerases of the present invention comprise or consist of the amino acid sequence as shown in SEQ ID NO: 3 (KlenTaq C12 DNA polymerase), SEQ ID NO: 4 (KlenTaq D9 DNA polymerase), SEQ ID NO: 5 (KlenTaq F4 DNA polymerase), SEQ ID NO: 6 (KlenTaq E9 DNA polymerase), SEQ ID NO: 7 (KlenTaq M1/M747K DNA polymerase), SEQ ID NO: 8 (Taq C12 DNA polymerase), SEQ ID NO: 9 (Taq D9 DNA polymerase), SEQ ID NO: 10 (Taq F4 DNA polymerase), SEQ ID NO: 11 (Taq E9 DNA polymerase), or SEQ ID NO: 12 (Taq M1/M747K DNA polymerase).

In a further aspect, the present invention relates to a nucleic acid, comprising a nucleotide sequence coding for a DNA polymerase according to the present invention.

In another aspect, the present invention relates to a vector comprising a nucleic acid according to the present invention. The term "vector" as used herein relates to any vehicle for the transportation of a nucleic acid into a cell. In particular, said term includes plasmid vectors, viral vectors, cosmid vectors, and artificial chromosomes, wherein plasmid vectors are particularly preferred. Preferably, plasmid vectors are suitable for expression of the DNA polymerases of the present invention in a prokaryotic or eukaryotic cell. Respective plasmid vectors are known in the art.

In a further aspect, the present invention relates to a host cell comprising the vector and/or the nucleic acid of the present invention. Suitable host cells that can be used for the recombinant expression of the DNA polymerases of the present invention are not particularly limited and are known in the art. They include for example suitable bacterial cells, yeast cells, plant cells, insect cells and mammalian cells.

In a further aspect, the present invention relates to a method for the generation of a DNA molecule, comprising the step of incubating a suitable template molecule with a DNA polymerase of the present invention.

Respective methods are not particularly limited and include all methods in which a DNA polymerase of the present invention is used to generate a DNA molecule. Suitable template molecules are not particularly limited and include naturally occurring or synthetic DNA or RNA molecules. As is known in the art, DNA polymerases need monomeric nucleotides for the synthesis of a new DNA molecule. These include naturally occurring and synthetic, as well as modified nucleotides such as 2'-deoxy nucleotides. Suitable conditions for generating a DNA molecule with the help of a DNA polymerase of the present invention, e.g. incubation duration and temperatures, are known in the art.

In a particular embodiment, the method of the present invention is a method for the reverse transcription of an RNA molecule into cDNA and the amplification of said cDNA by polymerase chain reaction (PCR) in one step (i.e. a "one-step method"), wherein said step comprises incubating said RNA molecule with a DNA polymerase of the present invention, wherein both of said reverse transcription and said amplification are mediated by said DNA polymerase.

In this method of the present invention, both the reverse transcription of the RNA molecule into cDNA and the amplification of said cDNA are mediated by the DNA polymerase of the present invention. Advantageously, on the one hand no further enzymes are required, and, preferably, no such enzymes are present in the reaction mixture, and on the other hand the method of the present invention does not require any manipulation of the reaction mixture after reverse transcription and prior to cDNA amplification. Accordingly, reverse transcription and amplification are conducted in one step (i.e. a "one-step method"). Advantageously, the reverse transcription step can be performed at elevated temperatures above 70° C. Suitable buffers for use in an RT-PCR reaction using a DNA polymerase of the present invention are not particularly limited and are known in the art. Further, suitable RT-PCR programs, i.e. regimes defining the duration and temperature of each individual step of the RT-PCR reaction, are not particularly limited and are known in the art.

In a particular example of the method of the present invention, said one-step method can simply consist of mixing a sample containing an RNA molecule with a suitable buffer comprising dNTPs, suitable primers and a DNA polymerase of the present invention, placing the reaction mixture in a PCR machine, and conducting a particular RT-PCR program, wherein no further sample manipulation steps are required.

In another particular embodiment, the method of the present invention is a method for the generation of a DNA molecule comprising modified nucleotides, comprising the step of incubating a suitable template molecule with a DNA polymerase of the present invention in the presence of said modified nucleotides.

In this method of the present invention, the term "modified nucleotide" is not particularly limited and includes any nucleotides that are modified in respect to the naturally occurring nucleotides. They include for example 2'-deoxy nucleotides.

Nevertheless, due to their increased thermostability and activity at temperatures above 70° C., the DNA polymerases of the present invention can also be advantageously used in any further methods, including two-step methods, methods for reverse transcription only, or methods that are performed in combination with further enzymes.

In a further aspect, the present invention relates to a kit comprising a DNA polymerase according to the present invention. In preferred embodiments, the kit of the present invention further comprises suitable buffers and/or suitable disposables and/or suitable enzymes.

In a final aspect, the present invention relates to the use of a DNA polymerase of the present invention for the generation of a DNA molecule. In a preferred embodiment, the present invention relates to the use of a DNA polymerase of the present invention for the reverse transcription of an RNA molecule into cDNA and the amplification of said cDNA by polymerase chain reaction (PCR). In another preferred embodiment, the present invention relates to the use of a DNA polymerase of the present invention for the generation of a DNA molecule comprising modified nucleotides.

The DNA polymerases of the present invention preferably comprise the mutation known from M747K DNA polymerase, i.e. the M747K mutation, as well as mutations known from M1 DNA polymerase, i.e. the mutations S515R and I638F, and optionally one or more of the mutations L322M, L459M, S739G, and E773G. However, the DNA polymerases of the present invention show characteristics with regard to their reverse transcriptase activity and their thermostability that significantly exceed what could have reasonably been expected from a combination of the mutations of the above known DNA polymerases (cf. Examples 1 and 2). Thus, the combination of the above mutations provides a surprising and unexpected synergistic effect resulting in DNA polymerases having superior advantageous properties.

The figures show:

FIG. 1: Three-dimensional tertiary structure of KlenTaq DNA polymerase showing the mutations sites of KlenTaq D9 DNA polymerase The positions of the mutations L459M, S515R, I638F, and M747K are shown.

Figure 2:
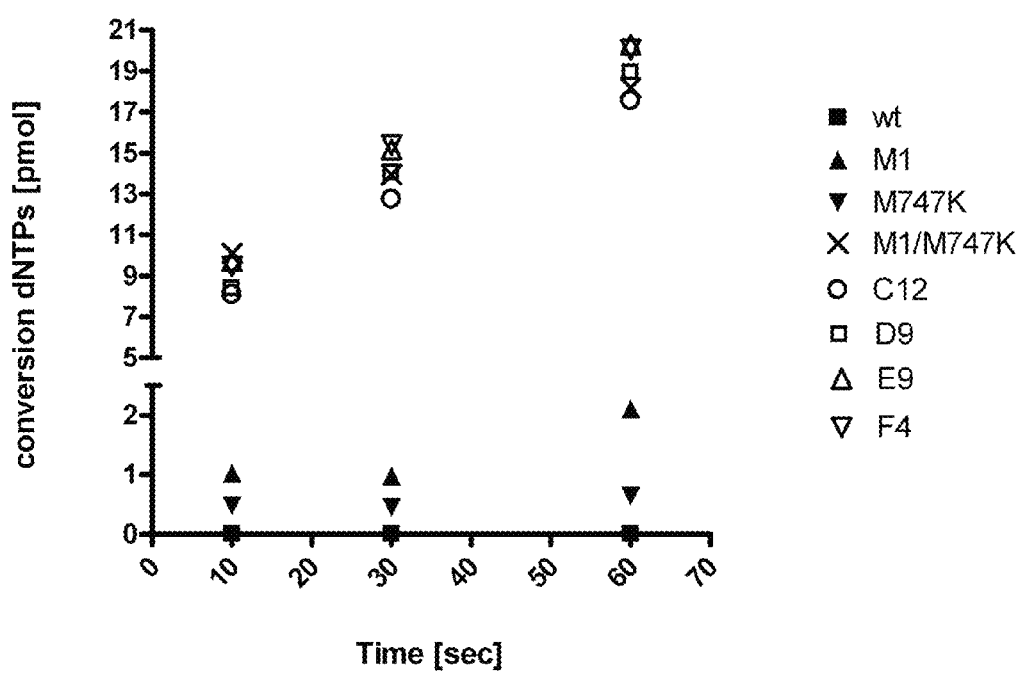

FIG. 2: Reverse transcriptase activity

Reverse transcriptase activity of the KlenTaq DNA polymerases of the present invention as measured by the conversion of dNTPs over time using an RNA template.

Figure 3:
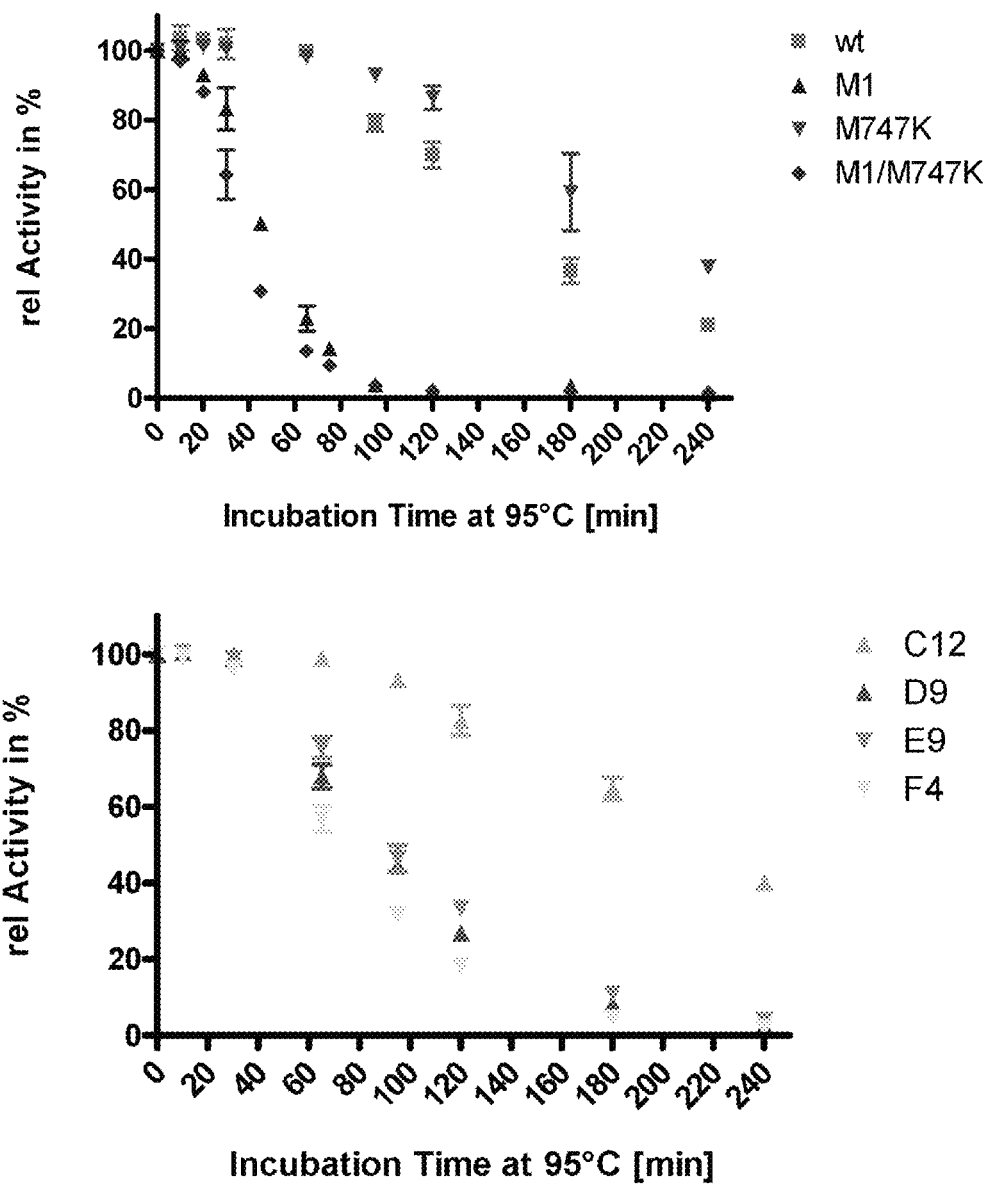

FIG. 3: Thermostability

Thermostability of the KlenTaq DNA polymerases of the present invention. Relative enzyme activity is measured after incubating the enzyme at 95° C. for the times indicated. Enzyme activity without incubating at 95° C. is set to 100%.

Figure 4:
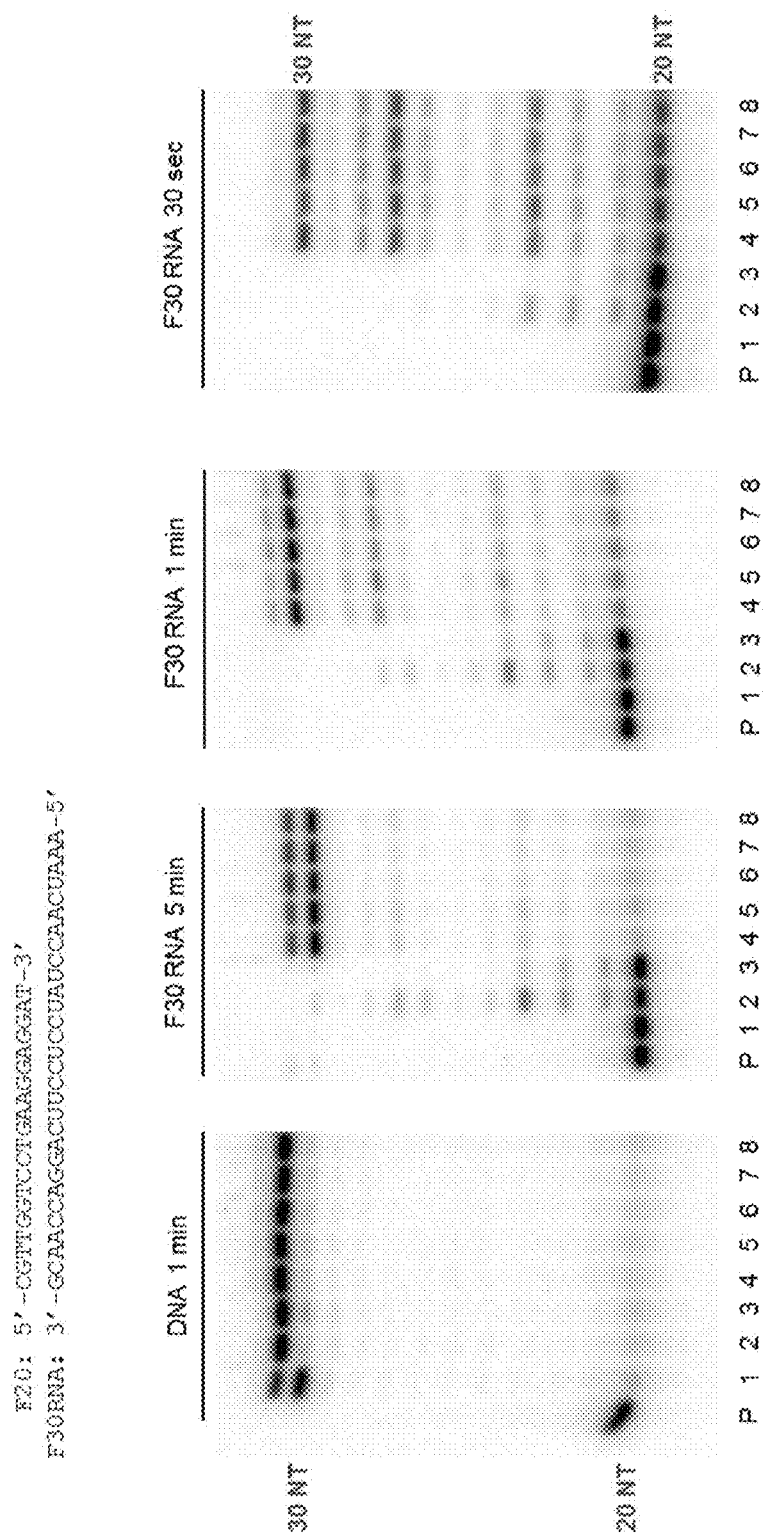

FIG. 4: Reverse transcription primer extension: KlenTaq DNA polymerases

Reverse transcription primer extension reactions with wild-type KlenTaq (lane 1), KlenTaq M1 (lane 2), KlenTaq M747K (lane 3), KlenTaq M1/M747K (lane 4), and different KlenTaq mutants (lane 5: C12, lane 6: D9, lane 7: E9, lane 8: F4). Reaction mixtures (20 µl) contained 50 mM Tris-HCl (pH 9.2), 16 mM $(NH_4)_2SO_4$, 0.1% Tween 20, 2.5 mM $MgCl_2$, 200 µM of each dNTP, 150 nM F20 primer, 225 nM F30 RNA and 25 nM of the respective KlenTaq DNA polymerase. Reaction mixtures were incubated at 72° C. P: Primer.

Figure 5:
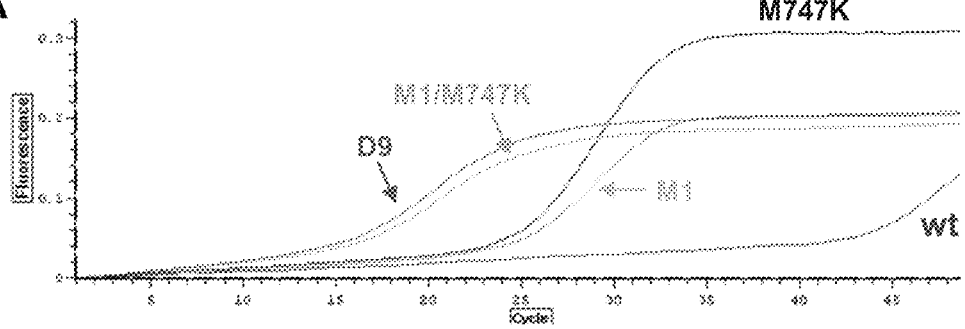
Figure 5:
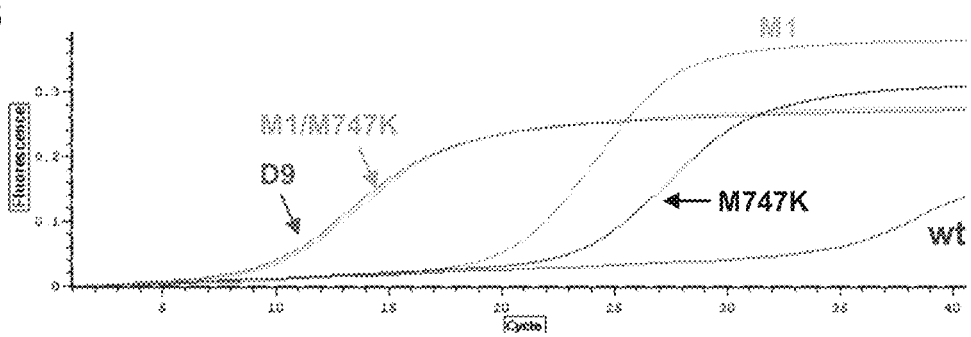

FIG. 5: Real-time RT-PCR

RT-PCR with wild-type KlenTaq, KlenTaq M1, KlenTaq M747K, KlenTaq M1/M747K and KlenTaq D9. (A) 50 pg/µl MS2 RNA (Roche) as template. (B) 40 pg/µl 16S- and 23S-rRNA (Roche) as template. Reaction mixtures (20 µl) contained 50 mM Tris-HCl (pH 9.2), 16 mM $(NH_4)_2SO_4$, 0.1% Tween 20, 2.5 mM $MgCl_2$, 200 µM of each dNTP, 100 nM of each primer, 0.6× SYBRgreen I, 5 nM of the respective KlenTaq DNA polymerase and the respective RNA template.

Figure 6:
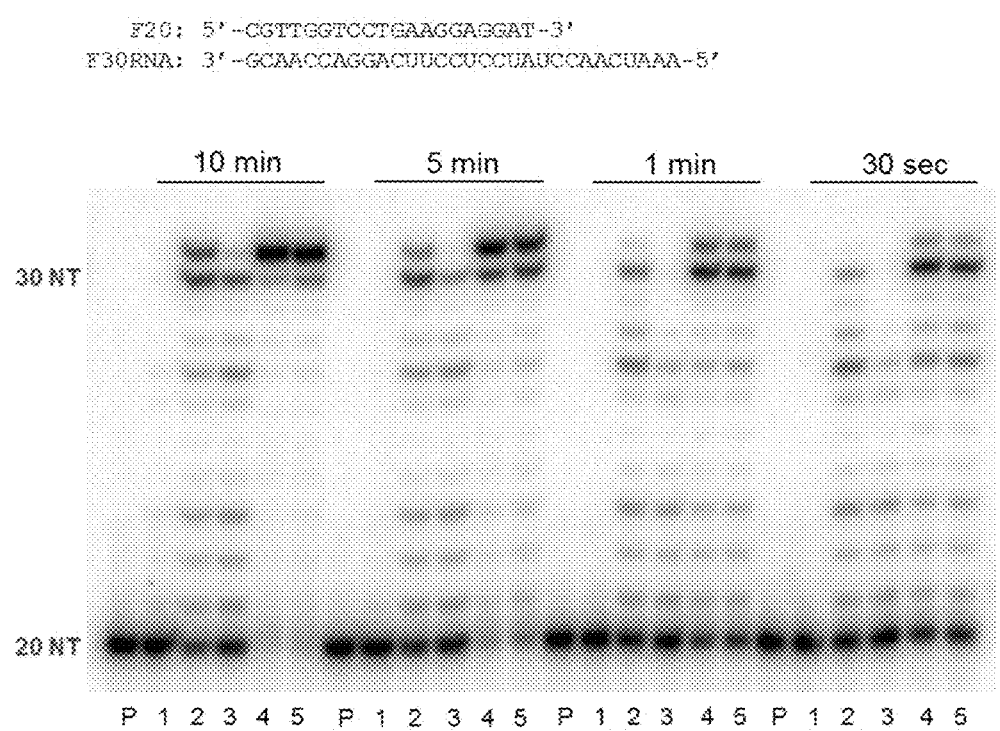

FIG. 6: Reverse transcription primer extension: Taq DNA polymerases

Reverse transcription primer extension reactions with wild-type Taq (lane 1), Taq M1 (lane 2), Taq M747K (lane 3), Taq M1/M747K (lane 4), and Taq D9 (lane 5). Reaction mixtures (20 µl) contained 50 mM Tris-HCl (pH 9.2), 16 mM $(NH_4)_2SO_4$, 0.1% Tween 20, 2.5 mM $MgCl_2$, 200 µM of each dNTP, 150 nM F20 primer, 225 nM F30 RNA and 25 nM of the respective Taq DNA polymerase. Reaction mixtures were incubated at 72° C. P: Primer.

Figure 7:
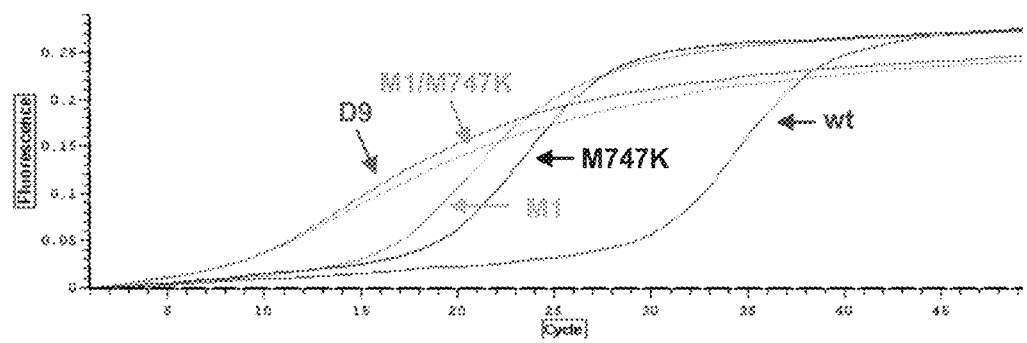

FIG. 7: Real-time RT-PCR

RT-PCR with wild-type Taq, Taq M1, Taq M747K, Taq M1/M747K and Taq D9. 50 pg/µl MS2 RNA (Roche) were used as template. Reaction mixtures (20 µl) contained 50 mM Tris-HCl (pH 9.2), 16 mM $(NH_4)_2SO_4$, 0.1% Tween 20, 2.5 mM $MgCl_2$, 200 µM of each dNTP, 100 nM of each primer, 0.6× SYBRgreen I, 5 nM of the respective Taq DNA polymerase and the respective RNA template.

Figure 8:
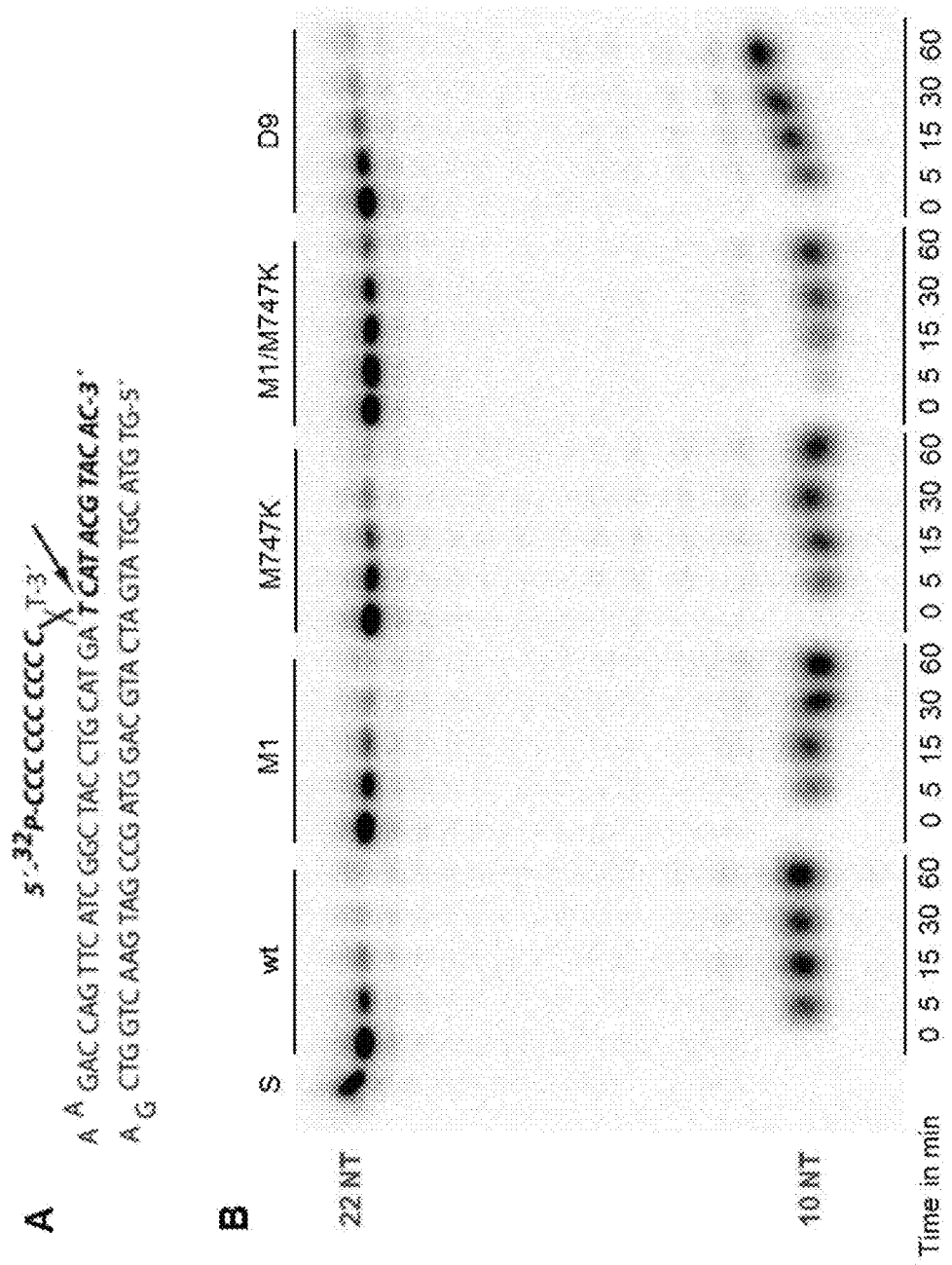

FIG. 8: Nuclease activity

Nuclease reactions with DNA polymerases derived from Taq DNA polymerase. (A) Hairpin structure of template and 22-nt substrate (bold). The arrow indicates the expected cleavage position. (B) Reaction products separated by denaturing PAGE. S: 22-nt substrate. Reaction mixtures (60 µl) contained 50 mM Tris-HCl (pH 9.2), 16 mM $(NH_4)_2SO_4$, 0.1% Tween 20, 2.5 mM $MgCl_2$, 50 nM of each dNTP, 150 nM 22-nt substrate, 225 nM template and 150 nM of the respective Taq DNA polymerase. Reaction mixtures were incubated at 30° C.

Figure 9:
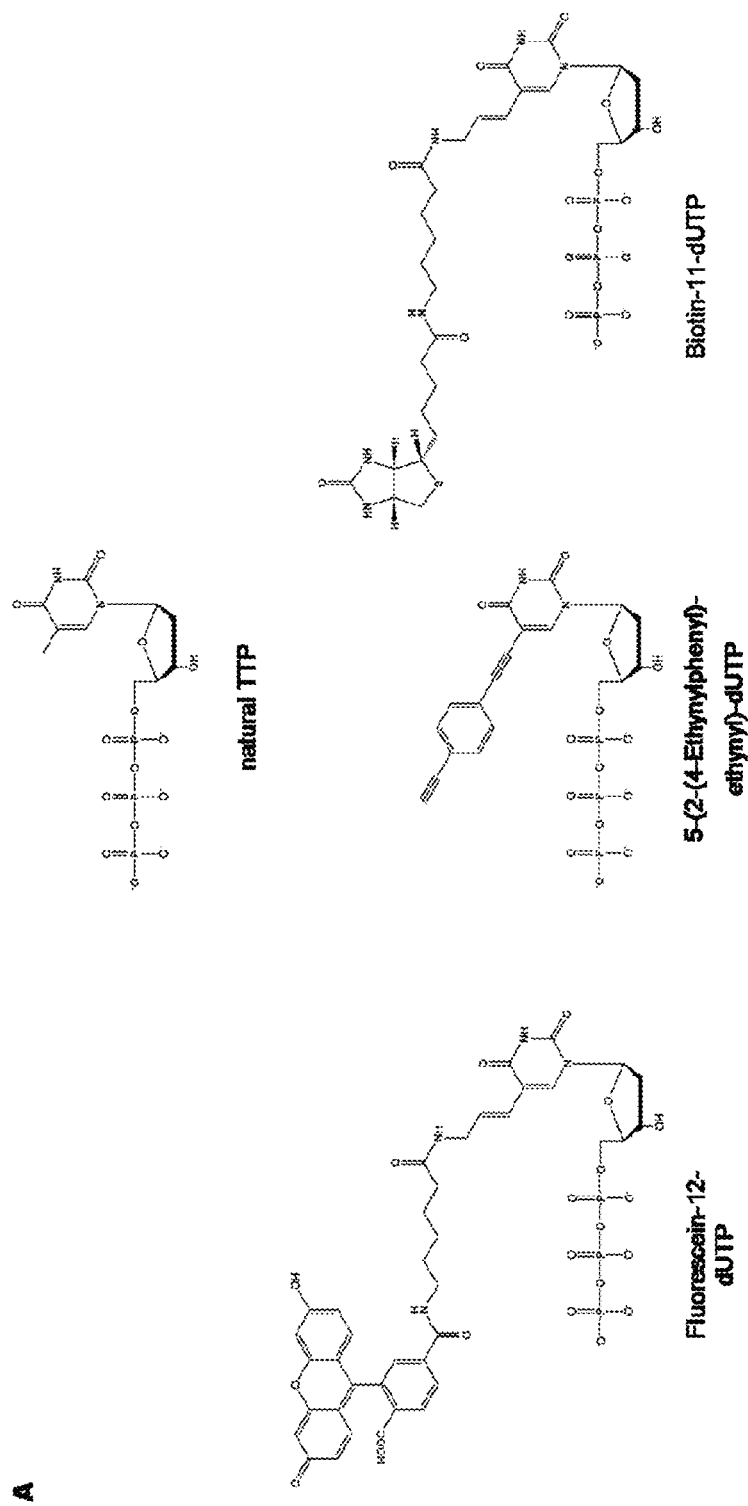
Figure 9:
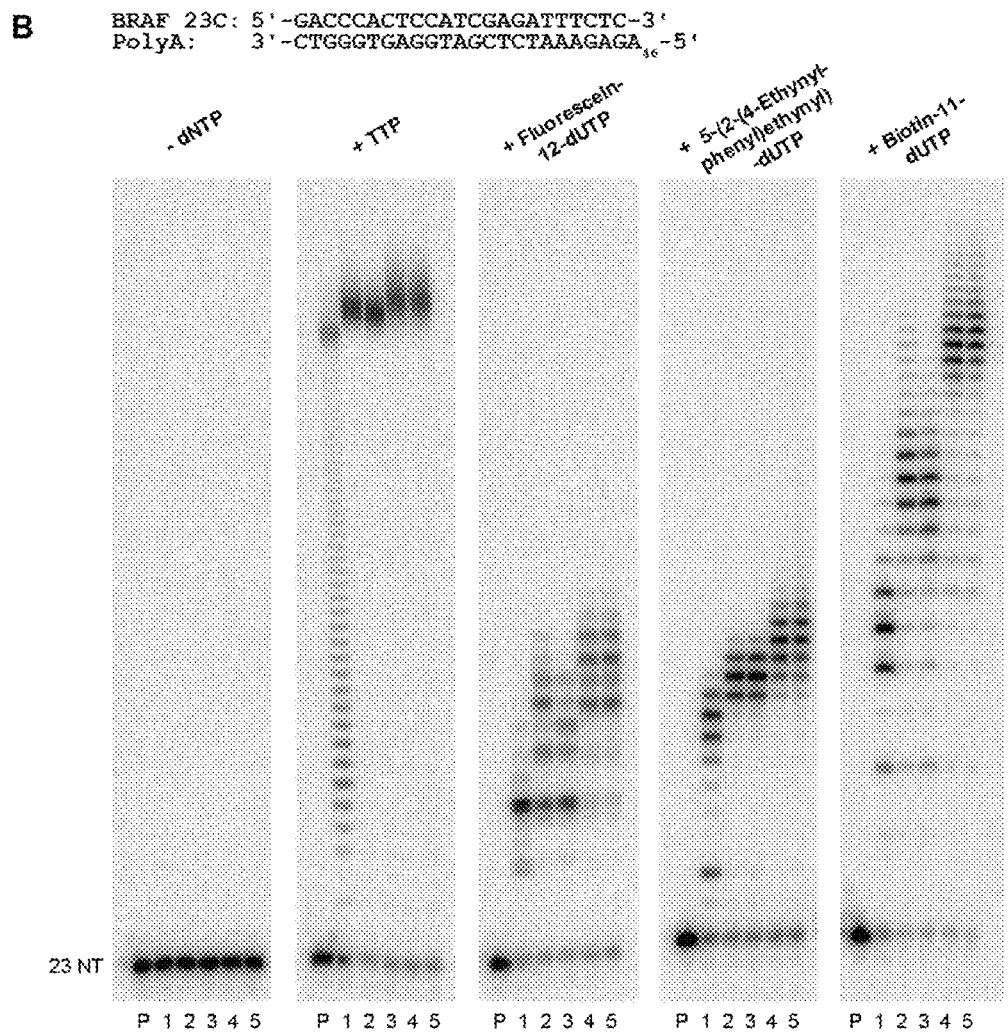

FIG. 9: Primer extension experiments in presence of either Fluorescein-12-dUTP, 5-(2-(4-Ethynylphenyl)ethynyl)-dUTP or Biotin-11-dUTP (A) Structures of Fluorescein-12-dUTP, 5-(2-(4-Ethynylphenyl)ethynyl)-dUTP and Biotin-11-dUTP.

(B) Primer extension reactions with wild-type KlenTaq (lane 1), KlenTaq M1 (lane 2), KlenTaq M747K (lane 3), KlenTaq M1/M747K (lane 4), and KlenTaq D9 (lane 5). Reaction mixtures (20 µl) contained 50 mM Tris-HCl (pH 9.2), 16 mM $(NH_4)_2SO_4$, 0.1% Tween 20, 2.5 mM $MgCl_2$, 100 µM of the respective dNTP, 150 nM BRAF23C primer, 200 nM template and 30 nM of the respective KlenTaq DNA polymerase. Reaction mixtures were incubated at 72° C. for 1 h (with natural TTP were incubated for 5 min). P: Primer.

The present invention will now be further illustrated in the following examples without being limited thereto.

EXAMPLES

Example 1

Reverse Transcriptase Activity of the DNA Polymerases of the Present Invention

The reverse transcriptase activity of the DNA polymerases of the present invention was determined by way of measuring the conversion of dNTPs over time using an RNA template.

In particular, reverse transcription primer extension reactions with wild-type KlenTaq, KlenTaq M1, KlenTaq M747K and KlenTaq DNA polymerases of the present invention were performed at 72° C. using 150 nM radioactively labeled primer F20 (5'-d(CGT TGG TCC TGA AGG AGG AT)-3'), 225 nM RNA template F30 (5'-AAA UCA ACC UAU CCU CCU UCA GGA CCA ACG-3'), 200 µM of each dNTP and 25 nM of the respective KlenTaq DNA polymerase in 50 mM Tris-HCl (pH 9.2), 16 mM $(NH_4)_2SO_4$, 0.1% Tween 20 and 2.5 mM $MgCl_2$. Reaction mixtures were stopped at 10, 30 and 60 sec, denatured at 95° C. for 5 min and separated using a 12% denaturing PAGE gel. Visualization was performed by phosphoimaging. The obtained bands were analyzed and their intensities transformed into dNTP conversion.

As can be taken from FIG. 2, the KlenTaq DNA polymerases of the present invention, comprising the mutation of M747K DNA polymerase and mutations of M1 DNA polymerase, have a significantly increased reverse transcriptase activity. In particular, KlenTaq M1 DNA polymerase polymerizes about 2 pmol dNTPs in 60 seconds on an RNA template, whereas M747K DNA polymerase polymerizes about 1 pmol dNTPs in the same time. However, the DNA polymerases of the present invention polymerize up to 20 pmol dNTPs in the same time. This increase greatly exceeds what would have reasonably been expected from the data for M1 and M747K DNA polymerases and demonstrates a surprising and unexpected synergistic effect of the respective mutations.

Example 2

Thermostability of the DNA Polymerases of the Present Invention

The thermostability of the KlenTaq DNA polymerases of the present invention has been determined by incubating said KlenTaq DNA polymerases at 95° C. for specific durations and determining their activity after said incubation.

In detail, KlenTaq DNA polymerases (20 nM) were incubated at 95° C. in 50 mM Tris-HCl (pH 9.2), 16 mM $(NH_4)_2SO_4$, 0.1% Tween 20 and 2.5 mM $MgCl_2$. At different time points, 15 µl samples were taken and stored on ice. Afterwards, primer extension reactions were performed at 72° C. for 5 min in a total volume of 15 µl. In particular, reaction mixtures containing primer, template, and dNTPs were mixed with 3.75 µl of the polymerase sample resulting in final concentrations of 150 nM radioactively labeled primer F23 (5'-d(CGT TGG TCC TGA AGG AGG ATA GG)-3'), 225 nM DNA template F33A (5'-d(AAA TCA ACC TAT CCT CCT TCA GGA CCA ACG TAC)-3'), 200 µM of each dNTP and 5 nM of the respective polymerase in 50 mM Tris-HCl (pH 9.2), 16 mM $(NH_4)_2SO_4$, 0.1% Tween 20 and 2.5 mM $MgCl_2$. Reaction mixtures were separated using a 12% denaturing PAGE gel and visualization was performed by phosphoimaging. The obtained bands were analyzed and their intensities transformed into dNTP conversion. Conversion of the reaction without heating the DNA polymerase sample was set to 100% activity.

As can be taken from FIG. 3, KlenTaq C12, KlenTaq D9, KlenTaq E9, and KlenTaq F4 DNA polymerases show increased thermostabilities as compared to M1 DNA polymerase.

Example 3

Reverse Transcriptase Activity of KlenTaq DNA Polymerases of the Present Invention in Primer Extension Experiments Reverse transcriptase activities of wild-type KlenTaq, KlenTaq M1, KlenTaq M747K and KlenTaq DNA polymerases of the present invention were compared in primer extension experiments using RNA as template and DNA as primer.

Reactions were performed at 72° C. using 150 nM radioactively labeled primer F20 (5'-d(CGT TGG TCC TGA AGG AGG AT)-3'), 225 nM RNA template F30 RNA (5'-AAA UCA ACC UAU CCU CCU UCA GGA CCA ACG-3'), 200 µM of each dNTP and 25 nM of the respective KlenTaq DNA polymerase in 50 mM Tris-HCl (pH 9.2), 16 mM $(NH_4)_2SO_4$, 0.1% Tween 20 and 2.5 mM $MgCl_2$. Reaction mixtures were stopped after 30 sec, 1 min and 5 min. After denaturation at 95° C. for 5 min, reaction mixtures were separated using a 12% denaturing PAGE gel. Visualization was performed by phosphoimaging. Control experiments were performed as described using DNA (5'-d(AAA TCA ACC TAT CCT CCT TCA GGA CCA ACG TAC)-3') as template and incubating for 1 min.

As can be taken from FIG. 4, the KlenTaq DNA polymerases of the present invention show increased reverse transcriptase activity as compared to KlenTaq M1 and KlenTaq M747K.

The KlenTaq DNA polymerases of the present invention extend the primer more efficiently at every time point and were able to produce full-length product even after 30 seconds. This experiment therefore corroborates the increased reverse-transcriptase activity of the DNA polymerases of the present invention resulting from the combination of both the M747K mutation and M1 mutations in one enzyme.

Example 4

Real-Time RT-PCR with KlenTaq DNA Polymerases of the Present Invention

Real-time RT-PCR experiments were performed with wild-type KlenTaq, KlenTaq M1, KlenTaq M747K, KlenTaq M1/M747K and KlenTaq D9.

Reaction mixtures (20 µl) contained 50 mM Tris-HCl (pH 9.2), 16 mM $(NH_4)_2SO_4$, 0.1% Tween 20, 2.5 mM $MgCl_2$, 200 µM of each dNTP, 100 nM of each primer (5'-d(ATC GCT CGA GAA CGC AAG TT)-3'; 5'-d(CG GAC TTC ATG CTG TCG GTG)-3'), 0.6× SYBRgreen I, 5 nM of the respective DNA polymerase and 50 pg/µl MS2 RNA (Roche).

First, reverse transcription was conducted using an initial denaturation step of 30 sec at 95° C., an annealing step at 55° C. for 35 sec and elongation for 7.5 min at 72° C. After denaturation for 1 min at 95° C., 50 PCR cycles were performed with 30 sec at 95° C., 35 sec at 55° C. and 40 sec at 72° C.

Reactions containing 40 pg/µl 16S- and 23S-rRNA from *E. coli* (Roche) were conducted as described above with the exception of an annealing temperature of 66° C., 40 PCR cycles and the respective primers (5'-d(CTG GCG GCA GGC CTA ACA CA)-3'; 5'-d(GCA GTT TCC CAG ACA TTA CT)-3'). Formation of double stranded DNA was detected by binding of SYBRgreen I and therefore by an increase in fluorescence. Correct product formation was confirmed by agarose gel analysis.

By using RNA as template, the KlenTaq DNA polymerases of the present invention show an increase in fluorescence after less cycles compared to KlenTaq M1 and KlenTaq M747K (shown in FIG. 5), indicating an increased RT-PCR activity at conditions were M1 shows very poor performance. This enables a broader application scope of the enzyme.

Example 5

Reverse Transcriptase Activity of Taq DNA Polymerases of the Present Invention in Primer Extension Experiments Reverse transcriptase activities of wild-type Taq, Taq M1, Taq M747K, Taq M1/M747K and Taq D9 were compared in primer extension experiments using RNA as template and DNA as primer.

Reactions were performed at 72° C. using 150 nM radioactively labeled primer F20 (5'-d(CGT TGG TCC TGA AGG AGG AT)-3'), 225 nM RNA template F30 (5'-AAA UCA ACC UAU CCU CCU UCA GGA CCA ACG-3'), 200 µM of each dNTP and 25 nM of the respective DNA polymerase in 50 mM Tris-HCl (pH 9.2), 16 mM $(NH_4)_2SO_4$, 0.1% Tween 20 and 2.5 mM $MgCl_2$. Reaction mixtures were stopped after 30 sec, 1 min, 5 min and 10 min. After denaturation at 95° C. for 5 min, reaction mixtures were separated using a 12% denaturing PAGE gel. Visualization was performed by phosphoimaging.

As can be taken from FIG. 6, the Taq DNA polymerases of the present invention show increased reverse transcriptase activity as compared to Taq M1 and Taq M747K.

The Taq DNA polymerases of the present invention extend the primer more efficiently at every time point. This experiment therefore corroborates the increased reverse-transcriptase activity of the Taq DNA polymerases of the present invention resulting from the combination of both the M747K mutation and M1 mutations in one enzyme.

Example 6

Real-Time RT-PCR with Taq DNA Polymerases of the Present Invention

Real-time RT-PCR experiments were performed with wild-type Taq, Taq M1, Taq M747K, Taq M1/M747K and Taq D9.

Reaction mixtures (20 µl) contained 50 mM Tris-HCl (pH 9.2), 16 mM $(NH_4)_2SO_4$, 0.1% Tween 20, 2.5 mM $MgCl_2$, 200 μM of each dNTP, 100 nM of each primer (5'-d(ATC GCT CGA GAA CGC AAG TT)-3'; 5'-d(CG GAC TTC ATG CTG TCG GTG)-3'), 0.6× SYBRgreen I, 5 nM of the respective DNA polymerase and 50 pg/μl MS2 RNA (Roche).

First, reverse transcription was conducted using an initial denaturation step of 30 sec at 95° C., an annealing step at 55° C. for 35 sec and elongation for 7.5 min at 72° C. After denaturation for 1 min at 95° C., 50 PCR cycles were then performed with 30 sec at 95° C., 35 sec at 55° C. and 40 sec at 72° C.

Formation of double stranded DNA was detected by binding of SYBRgreen I and therefore by an increase in fluorescence.

By using RNA as template, the Taq DNA polymerases of the present invention show an increase in fluorescence after less cycles (shown in FIG. 7), indicating a higher reverse-transcriptase PCR activity as compared to Taq M1 and Taq M747K activity at conditions were M1 and M747K show very poor performance. This enables a broader application scope of the enzyme.

Example 7

Nuclease Activity of DNA Polymerases Derived from Taq DNA Polymerase of the Present Invention Nuclease activities of Taq M1/M747K and Taq D9 were compared with nuclease activities of wild-type Taq, Taq M1 and Taq M747K. A stable DNA hairpin structure and a complementary, radioactively labeled substrate were used. Annealing of these two oligonucleotides leaves a displaced 5'-end and a frayed 3'-primer terminus which results in cleavage of the substrate oligonucleotide. Cleavage of this substrate was determined at different time points (0, 5, 15, 30, 60 min). Reaction mixtures (60 μl) contained 50 mM Tris-HCl (pH 9.2), 16 mM $(NH_4)_2SO_4$, 0.1% Tween 20, 2.5 mM $MgCl_2$, 50 nM of each dNTP, 150 nM 22-nt substrate (5'-d(CCC CCC CCC CTC ATA CGT ACA C)-3'), 225 nM template (5'-d(GTG TAC GTA TGA TCA TGC AGG TAG CCG ATG AAC TGG TCG AAA GAC CAG TTC ATC GGC TAC CTG CAT GAT)-3') and 150 nM of the respective Taq DNA polymerase. Reaction mixtures were incubated at 30° C.

Nuclease activities of Taq M1, Taq M747K and Taq D9 are comparable as can be seen in FIG. 8. Only Taq M1/M747K shows a slightly reduced nuclease activity, but nevertheless cleaves the substrate indicating a still active nuclease domain.

Example 8

Conversion of Modified 2'-Deoxynucleoside Triphosphates by KlenTaq DNA Polymerases of the Present Invention in Primer Extension Experiments The acceptance of 2'-deoxynucleoside triphosphates bearing a modification at the nucleobase was tested in primer extension experiments using wild-type KlenTaq, KlenTaq M1, KlenTaq M747K, KlenTaq M1/M747K and KlenTaq D9.

Reactions were performed at 72° C. using 150 nM radioactively labeled primer BRAF23C (5'-d(GAC CCA CTC CAT CGA GAT TTC TC)-3'), 200 nM template (5'-d($A_{46}$ GA GAA ATC TCG ATG GAG TGG GTC)-3'), 100 μM of the respective dNTP and 30 nM of KlenTaq DNA polymerase in 50 mM Tris-HCl (pH 9.2), 16 mM $(NH_4)_2SO_4$, 0.1% Tween 20 and 2.5 mM $MgCl_2$. Reaction mixtures were stopped after 5 min in case of TTP and after 1 h in all other cases, denatured at 95° C. for 5 min and separated using a 12% denaturing PAGE gel. Visualization was performed by phosphoimaging. Control experiments were performed as described using either no dNTP or natural TTP instead of the modified dNTPs.

As can be taken from FIG. 9, the KlenTaq DNA polymerases of the present invention show a significantly increased acceptance of modified dNTPs as compared to KlenTaq M1 and KlenTaq M747K. In particular, a DNA template bearing only 2'-deoxyadenosine residues after the primer binding site was used to call for the multiple incorporation of either Fluorescein-12-dUMP (Thermo Scientific), 5-(2-(4-Ethynylphenyl)ethynyl)-dUMP (Obeid S. et al., Chem. Commun., 2012, Interactions of non-polar and "Click-able" nucleotides in the confines of a DNA polymerase active site; DOI: 10.1039/C2CC34181F) or Biotin-11-dUMP (Jena Bioscience).

Positive controls show formation of full length product after 5 min with all tested DNA polymerases. Incubation with the modified substrates yields no full length product, but all DNA polymerases are able to incorporate several modified nucleotides. However, KlenTaq M1/M747K and KlenTaq D9 show an increased acceptance of Fluorescein-12-dUTP and 5-(2-(4-Ethynylphenyl)ethynyl)-dUTP compared to the parental enzymes KlenTaq M1 and KlenTaq M747K. In presence of Biotin-11-dUTP KlenTaq M1 and KlenTaq M747K are able to incorporate around 10 modified nucleotides in a row. However, the DNA polymerases of the present invention KlenTaq M1/M747K and KlenTaq D9 yield products displaying up to 18 incorporated, modified nucleotides and are also able to synthesize even longer products of up to 25 incorporated nucleotides.

All three experiments show that KlenTaq D9 and KlenTaq M1/M747K possess increased incorporation and extension efficiencies of modified substrates compared to KlenTaq M1 and KlenTaq M747K.

The invention claimed is:

1. An isolated DNA polymerase derived from wild-type *Thermus aquaticus* (Taq) DNA polymerase, comprising the mutations S515R, I638F, and M747K with regard to the amino acid sequence of wild-type Taq DNA polymerase of SEQ ID NO: 1, wherein the DNA polymerase derived from wild-type *Thermus aquaticus* (Taq) DNA polymerase has an amino acid sequence that is more than 70%, more than 80%, more than 85%, more than 90%, more than 92%, more than 94%, more than 96%, more than 97%, more than 98% or more than 99% identical to SEQ ID NO:1.

2. The isolated DNA polymerase of claim 1, comprising the amino acid sequence of SEQ ID NO: 1 comprising the mutations S515R, I638F, and M747K.

3. The isolated DNA polymerase of claim 1, comprising the amino acid sequence corresponding to amino acids 293 to 832 of SEQ ID NO: 1 comprising the mutations S515R, I638F, and M747K.

4. The isolated DNA polymerase of claim 3, comprising the amino acid sequence of SEQ ID NO: 2 comprising the mutations S515R, I638F, and M747K with regard to the amino acid sequence of wild type Taq DNA polymerase of SEQ ID NO:1.

5. The isolated DNA polymerase of claim 1, further comprising one or more mutations, selected from the group consisting of L322M, L459M, S739G, E773G, and L789F with regard to SEQ ID NO: 1.

6. The isolated DNA polymerase of claim 5, comprising the mutation L459M with regard to SEQ ID NO: 1.

7. The isolated DNA polymerase of claim 5, comprising the mutations L322M and L459M with regard to SEQ ID NO: 1.

8. The isolated DNA polymerase of claim 5, comprising the mutations L322M, L459M, and E773G with regard to SEQ ID NO: 1.

9. The isolated DNA polymerase of claim 5, comprising the mutations L322M, L459M, S739G, and E773G with regard to SEQ ID NO: 1.

10. The isolated DNA polymerase of claim 1, comprising the amino acid sequence of any one of SEQ ID NOs: 3 to 12.

11. An isolated nucleic acid comprising a nucleotide sequence coding for a DNA polymerase of claim 1.

12. A vector comprising the nucleic acid of claim 11.

13. A host cell comprising the vector of claim 12.

14. A method for the generation of a DNA molecule, comprising the step of incubating a suitable template molecule with the DNA polymerase of claim 1.

15. The method of claim 14, wherein said method is a method for the reverse transcription of an RNA molecule into cDNA and the amplification of said cDNA by polymerase chain reaction (PCR) in one step, wherein said step comprises incubating said RNA molecule with the DNA polymerase of claim 1, wherein both of said reverse transcription and said amplification are mediated by said DNA polymerase.

16. The method of claim 14, wherein said method is a method for the generation of a DNA molecule comprising modified nucleotides, comprising the step of incubating a suitable template molecule with the DNA polymerase of claim 1 in the presence of said modified nucleotides.

17. A kit comprising the DNA-polymerase of claim 1.

18. A host cell comprising the nucleic acid of claim 11.

* * * * *